United States Patent
Clavero et al.

(10) Patent No.: US 11,741,383 B2
(45) Date of Patent: *Aug. 29, 2023

(54) SYSTEMS AND METHODS TO SUGGEST SOURCE INGREDIENTS USING ARTIFICIAL INTELLIGENCE

(71) Applicant: NotCo Delaware, LLC, Santiago (CL)

(72) Inventors: Francisco Clavero, Santiago (CL); Kyohei Kaneko, Oakland, CA (US); Héctor Henriquez, Santiago (CL); Catalina Donoso, Santiago (CL); Aadit Patel, Burlingame, CA (US)

(73) Assignee: NotCo Delaware, LLC, Santiago (CL)

( * ) Notice: Subject to any disclaimer, the term of this patent is extended or adjusted under 35 U.S.C. 154(b) by 0 days.

This patent is subject to a terminal disclaimer.

(21) Appl. No.: 17/720,684

(22) Filed: Apr. 14, 2022

(65) Prior Publication Data
US 2023/0134489 A1 May 4, 2023

Related U.S. Application Data

(63) Continuation of application No. 17/519,210, filed on Nov. 4, 2021, now Pat. No. 11,373,107.

(51) Int. Cl.
*G06N 20/10* (2019.01)
*G06N 5/04* (2023.01)
(Continued)

(52) U.S. Cl.
CPC ............ *G06N 5/04* (2013.01); *G06F 18/214* (2023.01); *G06F 18/2178* (2023.01); *G06N 3/08* (2013.01);
(Continued)

(58) Field of Classification Search
CPC ........ G06N 5/04; G06N 20/00; G06K 9/6256; G06K 9/6263
See application file for complete search history.

(56) References Cited

U.S. PATENT DOCUMENTS 5,305,076 A 4/1994 Inoue et al.
8,044,354 B2 10/2011 Werner et al.
(Continued)

FOREIGN PATENT DOCUMENTS

WO 2004083451 A1 9/2004
WO 2013052824 A1 4/2013
(Continued)

OTHER PUBLICATIONS

International Searching Authority, "Search Report" for the application No. PCT/US2022/024636, dated Apr. 28, 2022, 6 pages.
(Continued)

*Primary Examiner* — Lam S Nguyen
(74) *Attorney, Agent, or Firm* — Haverstock & Owens, A Law Corporation

(57) ABSTRACT

Techniques to suggest a set of source ingredients that can be used to recreate functional properties of a target food item, using artificial intelligence, are disclosed. A computer model determines, for the target food item, an ingredient quantities vector and an ingredient inclusion vector based on a matrix of chemical compound source ingredient vectors of all source ingredients. The ingredient inclusion vector indicates which source ingredients from a plurality of source ingredients to include in the ingredient set, and the ingredient quantities vector indicates the quantity or amount of each source ingredient such that a corresponding volatile profile of the ingredient set is similar to that of the target food item. A volatile profile for the ingredient set, which is determined from the matrix of chemical compound source ingredient vectors, the ingredient inclusion vector, and the ingredient quantities vector, mimics the target food item's volatile profile.

20 Claims, 6 Drawing Sheets

(51) Int. Cl.
  *G16C 20/00* (2019.01)
  *G16C 60/00* (2019.01)
  *G06N 3/08* (2023.01)
  *G16C 20/70* (2019.01)
  *G06F 18/214* (2023.01)
  *G06F 18/21* (2023.01)

(52) U.S. Cl.
  CPC .............. *G16C 20/00* (2019.02); *G16C 20/70* (2019.02); *G16C 60/00* (2019.02)

(56) References Cited

U.S. PATENT DOCUMENTS

| | | |
|---|---|---|
| 8,419,433 B2 | 4/2013 | Do et al. |
| 8,647,121 B1 | 2/2014 | Witlin et al. |
| 8,775,341 B1 | 7/2014 | Commons |
| 9,513,167 B2 | 12/2016 | Hargreaves et al. |
| 9,519,620 B1 | 12/2016 | Pinel et al. |
| 9,841,897 B2 | 12/2017 | Palmer et al. |
| 10,325,181 B2 | 6/2019 | Xu et al. |
| 10,515,715 B1 | 12/2019 | Pappas et al. |
| 10,915,818 B1 | 2/2021 | Patel et al. |
| 10,957,424 B1 | 3/2021 | Navon et al. |
| 10,962,473 B1 | 3/2021 | O'Hara et al. |
| 10,970,621 B1 | 4/2021 | Pichara et al. |
| 10,984,145 B1 | 4/2021 | Hutchinson et al. |
| 10,993,465 B2 | 5/2021 | Pichara et al. |
| 11,164,069 B1 | 11/2021 | Korsunsky et al. |
| 11,164,478 B2 | 11/2021 | Pichara et al. |
| 11,205,101 B1 | 12/2021 | Garcia et al. |
| 11,348,664 B1 | 5/2022 | Kaneko et al. |
| 11,373,107 B1 | 6/2022 | Clavero et al. |
| 11,404,144 B1 | 8/2022 | Kang et al. |
| 11,514,350 B1 | 11/2022 | Kaneko et al. |
| 2002/0184167 A1 | 12/2002 | McClanahan |
| 2003/0157725 A1 | 8/2003 | Franzen et al. |
| 2004/0153250 A1 | 8/2004 | Hurst et al. |
| 2005/0143936 A1 | 6/2005 | Laughlin et al. |
| 2007/0139667 A1 | 6/2007 | Russell et al. |
| 2009/0055247 A1 | 2/2009 | Jackson |
| 2011/0020518 A1 | 1/2011 | Delort et al. |
| 2012/0082362 A1 | 4/2012 | Diem et al. |
| 2012/0328178 A1 | 12/2012 | Remiszewski et al. |
| 2013/0149679 A1 | 6/2013 | Tokuda et al. |
| 2013/0221222 A1 | 8/2013 | Baiz et al. |
| 2013/0222406 A1 | 8/2013 | Wolfe et al. |
| 2016/0025569 A1 | 1/2016 | Hargreaves et al. |
| 2016/0110584 A1 | 4/2016 | Remiszewski et al. |
| 2016/0358043 A1 | 12/2016 | Mu et al. |
| 2017/0116517 A1 | 4/2017 | Chee et al. |
| 2017/0139902 A1 | 5/2017 | Byron et al. |
| 2017/0220558 A1 | 8/2017 | Pinel et al. |
| 2017/0238590 A1 | 8/2017 | Bansal-Mutalik et al. |
| 2017/0345185 A1 | 11/2017 | Byron et al. |
| 2018/0101784 A1 | 4/2018 | Rolfe et al. |
| 2018/0192680 A1 | 7/2018 | Fraser et al. |
| 2018/0203921 A1 | 7/2018 | Privault et al. |
| 2018/0293489 A1 | 10/2018 | Eyster et al. |
| 2018/0357299 A1 | 12/2018 | Miranda et al. |
| 2019/0171707 A1 | 6/2019 | Rapaport |
| 2019/0200797 A1 | 7/2019 | Diao et al. |
| 2019/0228855 A1 | 7/2019 | Leiter et al. |
| 2019/0228856 A1 | 7/2019 | Leiter et al. |
| 2019/0295440 A1 | 9/2019 | Hadad |
| 2020/0268032 A1 | 8/2020 | Okuyama et al. |
| 2020/0309746 A1 | 10/2020 | Sakai |
| 2020/0365053 A1 | 11/2020 | Pichara et al. |
| 2021/0027379 A1 | 1/2021 | Zhu et al. |
| 2021/0117665 A1 | 4/2021 | Simantov et al. |

FOREIGN PATENT DOCUMENTS

| | | |
|---|---|---|
| WO | 2016010097 A1 | 1/2016 |
| WO | 2017070605 A1 | 4/2017 |
| WO | 2020237214 A1 | 11/2020 |
| WO | 2021026083 A1 | 2/2021 |
| WO | 2021071756 A1 | 4/2021 |
| WO | 2022010503 A1 | 1/2022 |
| WO | 2022010544 A1 | 1/2022 |
| WO | 2022035464 A1 | 2/2022 |
| WO | 2022098381 A1 | 5/2022 |
| WO | 2022/235326 A1 | 11/2022 |
| WO | 2022/240439 A1 | 11/2022 |

OTHER PUBLICATIONS

International Searching Authority, "Search Report" in application No. PCT/US2022/024640, dated May 5, 2022, 6 pages.

United States Patent Office, "Notice of Allowance", in U.S. Appl. No. 17/518,963, dated May 11, 2022, 7 pages.

Hahladakis et al., "An Overview of Chemical Additives Present in Plastics: Migration, Release, Fate and Environmental Impact During Their Use, Disposal and Recycling", Journal of Hazardous Materials 344 (2018), pp. 179-199.

Zou et al., "Regularization and Variable Selection via the Elastic Net", Department of Statistics, Stanford University, dated Dec. 5, 2003, 29 pages.

Bowman et al., "Generating Sentences from a Continuous Space", May 2016.

Rudinger et al., Skip-Prop: Representing Sentences with One Vector Pre Proposition, 12th International Conference on Computational Semantics, dated 2017, 7 pages.

Karamanolakis et al., "Item Recommendation with Variational Autoencoders and Heterogeneous Priors", DLRS, dated Oct. 2018, 5 pages.

Eating bird food, "Vegan "Chicken" Salad", https://www.eatingbirdfood.com/simple-vegan-mock-chicken-salad/, Apr. 5, 2017, downloaded Mar. 11, 2021. (Year: 2017).

Rong, Xin. word2vec Parameter Learning Explained. arXiv:1411.2738v4 [cs.CL] Jun. 5, 2016. (Year: 2016).

Salvador, Amaia, et al. "Learning cross-modal embeddings for cooking recipes and food images." Proceedings of the IEEE conference on computer vision and pattern recognition. 2017. (Year: 2017).

David Xu, "Machine Learning for Flavor Development," Bachelor's Thesis, Harvard College, School of Engineering and Applied Sciences, Apr. 5, 2019, 69 pages.

Hattab et al., Application of an Inverse Neural Network Model for the Identification of Optimal Amendment to Reduce Copper Toxicity in Phytoremediated Contaminated Soils, Journal of Geochemical Exploration, Elsevier, 2014, 136, pp. 14-23, 2014. (Year: 2014).

Kieaibi E., Determination of Protein Secondary Structure from Infrared Spectra Using Partial Least-Squares Regression, 9 pages, 2016 (Year: 2016).

Yang et al., "Obtaining information about protein secondary structures in aqueous solution using Fourier transform IR spectroscopy", Published online Feb. 5, 2015, nature protocols, 16 pages.

XGBoost, "Python Package Introduction", https://xgboost.readthedocs.io/en/latest/python/python_intro.html, last viewed on Nov. 5, 2020, 5 pages.

GitHub.com, "CMBI/DSSP", https://github.com/cmbi/dssp, last viewed on Nov. 5, 2020. 4 pages.

Wilcox et al., "Determination of Protein Secondary Structure from Infrared Spectra Using Partial Least-Squares Regression", dated 2016 American Chemical Society, 9 pages.

Sigma-Aldrich, "IR Spectrum Table and Chart", https://www.sigmaaldrich.com/technical-documents/articles/biology/ir-spectrum-table.html, last viewed on Nov. 5, 2020, 6 pages.

SciPy.org, "scipy.signal.savgol_filter", https://docs.scipy.org/doc/scipy/reference/generated/scipy.signal.savgol_filter.html, last viewed on Nov. 5, 2020, 3 pages.

SciPy.org, "scipy.integrate.simps", https://docs.scipy.org/doc/scipy/reference/generated/scipy.integrate.simps.html, last viewed on Nov. 5, 2020, 2 pages.

Scikitlearn.org, "sklearn.neighbors.KNeighborsRegressor", https://scikit-learn.org/stable/modules/generated/sklearn.neighbors.KNeighborsRegressor.html, last viewed on Nov. 5, 2020, 5 pages.

(56) References Cited

OTHER PUBLICATIONS

Scikitlearn.org, "sklearn.model_selection.GridSearchCV", https://scikit-learn.org/stable/modules/generated/sklearn.model_selection.GridSearchCV.html, last viewed on Nov. 5, 2020, 7 pages.
Scikitlearn.org, "sklearn.linear_model.lasso", https://scikit-learn.org/stable/modules/generated/sklearn.linear_model.Lasso.html, last viewed on Nov. 5, 2020, 6 pages.
Scikitlearn.org, "sklearn.cross_decomposition.PLSRegression", https://scikit-learn.org/stable/modules/generated/sklearn.cross_decomposition.PLSRegression.html , last viewed on Nov. 5, 2020, 5 pages.
Scikitlearn.org, "3.2.4.1.3. sklearn.linear_model.LassoCV", https://scikit-learn.org/stable/modules/generated/sklearn.linear_model.LassoCV.html, last viewed on Nov. 5, 2020, 6 pages.
ProDry, "DSSP Tools", http://prody.csb.pitt.edu/manual/reference/proteins/dssp.html, last viewed on Nov. 5, 2020, 2 pages.
Cao et al., "Optimization of Formulations Using Robotic Experiments Driven by Machine Learning DoE", Cell Reports Physical Science, Jan. 20, 2021, 17 pages.
Cromwell et al., "Computational Creativity in the Culinary Arts", Proceedings of the Twenty-Eighth International Florida Artificial Intelligence Research Society Conference, dated 2015, 5 pages.
Park et al., "FlavorGraph: a large-scale food-chemical grpah for generating food representations and recommending food pairings", Scientific Reports: nature Research, vol. 11, Jan. 13, 2021, 13 pages.
Yuan et al., "An Inductive Content-Augmented Network Embedding Model for Edge Artificial Intelligence", IEEE Transaction on Industrial Informatics, vol. 15 No. 7, Jul. 2019, pp. 4295-4305.
Hodgkin, "The Castlemaine Project: Development of an AI-based Drug Design Support System", Molecular Modelling and Drug Design, 1994, pp. 137-169.
Peiretti et al., "Artificial Intelligence: The Future for Organic Chemistry?", ACS Omega, 2018, 3 (10), pp. 13263-13266.
Fromm et al., "A Vector Space model for Neural Network Functions: Inspirations from Similarities between the Theory of Connectivity and the Logarithmic Time Course of Word Production", Frontiers in Systems Neuroscience, Aug. 28, 2020, 10 pages.
United States Patent Office, "Office Action", in U.S. Appl. No. 17/351,069, dated Jan. 11, 2022, 10 pages.
United States Patent Office, "Office Action", in U.S. Appl. No. 17/351,069, dated Feb. 17, 2022, 10 pages.
United States Patent Office, "Office Action", in U.S. Appl. No. 17/518,963, dated Feb. 17, 2022, 17 pages.
United States Patent Office, "Office Action", in U.S. Appl. No. 17/518,963, dated Mar. 23, 2022, 16 pages.
United States Patent Office, "Notice of Allowance", in U.S. Appl. No. 17/351,069, dated Mar. 28, 2022, 8 pages.
United States Patent Office, "Notice of Allowance", in U.S. Appl. No. 17/519,210, dated Apr. 4, 2022, 8 pages.
Paul, Rahl, "Classifying Cooking Object's State using a Tuned VGG Convolutional Neural Netwrok," May 2018, 5 pages.
De Clercq et al., "Data-Driven Recipe Completion Using Machine Learning Methods," Trends in Food Science & Technology 49 (2016), Dec. 2015, p. 1-13.
Pinel et al., Chapter 16: A Culinary Computational Creativity System, Computational Creativity Research: Towards Creative Machines, Jan. 2014, pp. 327-346.

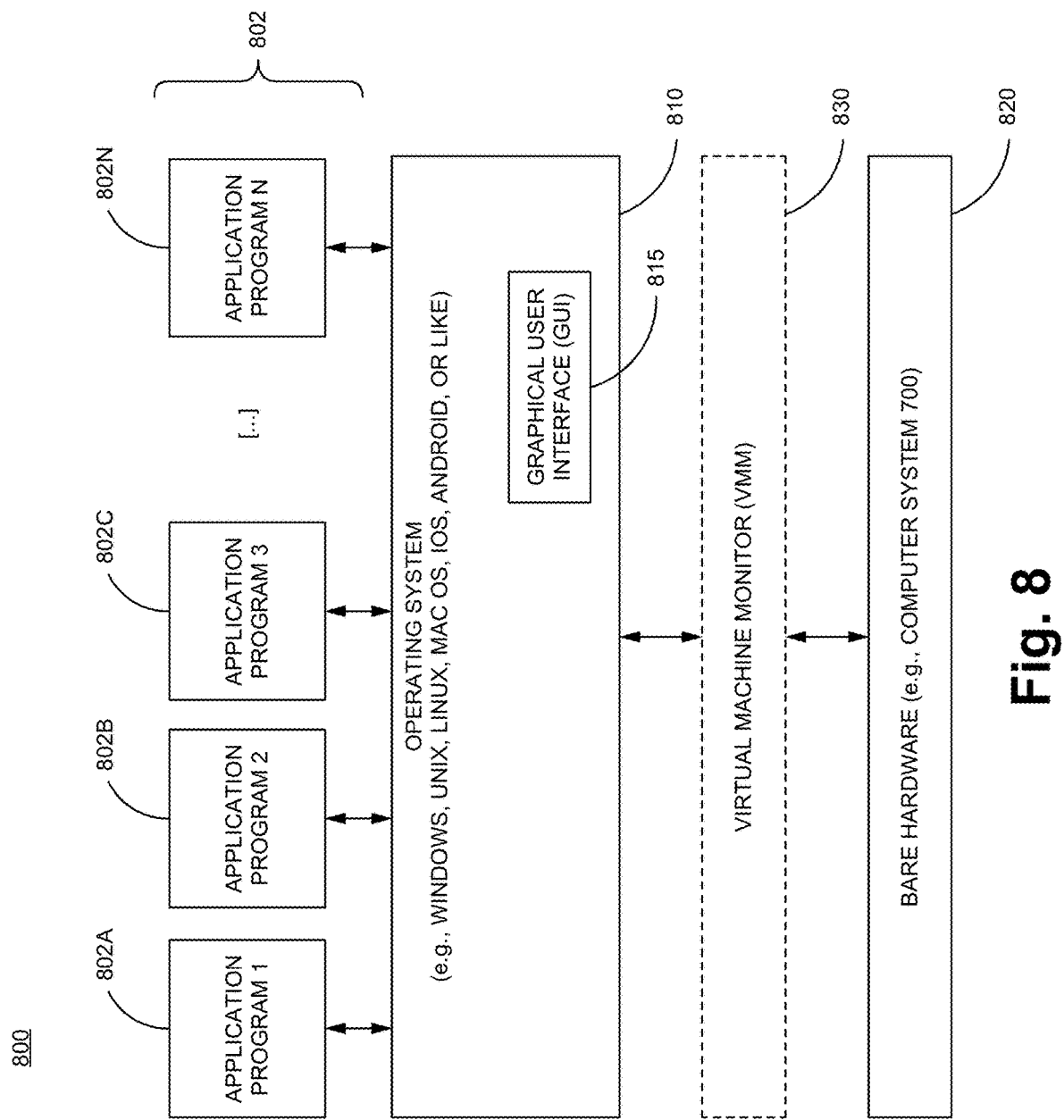

SYSTEMS AND METHODS TO SUGGEST SOURCE INGREDIENTS USING ARTIFICIAL INTELLIGENCE

BENEFIT CLAIM

This application is a continuation of U.S. non-provisional application Ser. No. 17/519,210, titled "Systems and Methods to Suggest Source Ingredients Using Artificial Intelligence," filed Nov. 4, 2021, entire contents of which are hereby incorporated herein by reference for all purposes as if fully set forth herein. The applicant(s) hereby rescind any disclaimer of claim scope in the parent application(s) or the prosecution history thereof and advise the USPTO that the claims in this application may be broader than any claim in the parent application(s).

TECHNICAL FIELD

One technical field of the present disclosure is artificial intelligence and machine learning, as applied to food. Another technical field is food science. The disclosure relates, in particular, to use of machine learning to suggest chemical compounds with desired functional properties or that may be used to recreate functional properties of target chemical compounds that are present in products, such as food items. The disclosure also relates to suggesting sets of source ingredients that may be used to recreate functional properties of target food items.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Today, many negative consequences of use of animals in the food industry are known, such as deforestation, pollution, human health conditions, and allergies, among others. In contrast, a plant-based diet is associated with improved health and well-being and reduces risk of diseases. Not only is a plant-based diet only good for human health but it is also good for the Earth's health. Research has shown that production of plant-based food items generates less greenhouse emissions and require less energy, water, and land than production of animal-based food items. There are plant alternatives to animal-based food items. For example, plant alternatives to meat include veggie burgers and other vegan meat food items. However, these alternatives do not match the taste and texture of meat.

Accordingly, there is a need for improved techniques to mimic a food item, such as an animal-based food item, by matching sensory attributes as much as possible. Unfortunately, many techniques for development of new foods rely upon time-consuming, inaccurate, manual laboratory work in which different ingredients are combined in different ways and tested. These approaches are inefficient, involve extensive time to develop a single successful food formula, and waste physical resources.

SUMMARY

The appended claims may serve as a summary of the invention.

BRIEF DESCRIPTION OF THE FIGURES

The present invention is illustrated by way of example, and not by way of limitation, in the figures of the accompanying drawings and in which like reference numerals refer to similar elements and in which:

FIG. 8 illustrates a block diagram of a basic software system for controlling the operation of a computing device.

DETAILED DESCRIPTION

Figure 1:
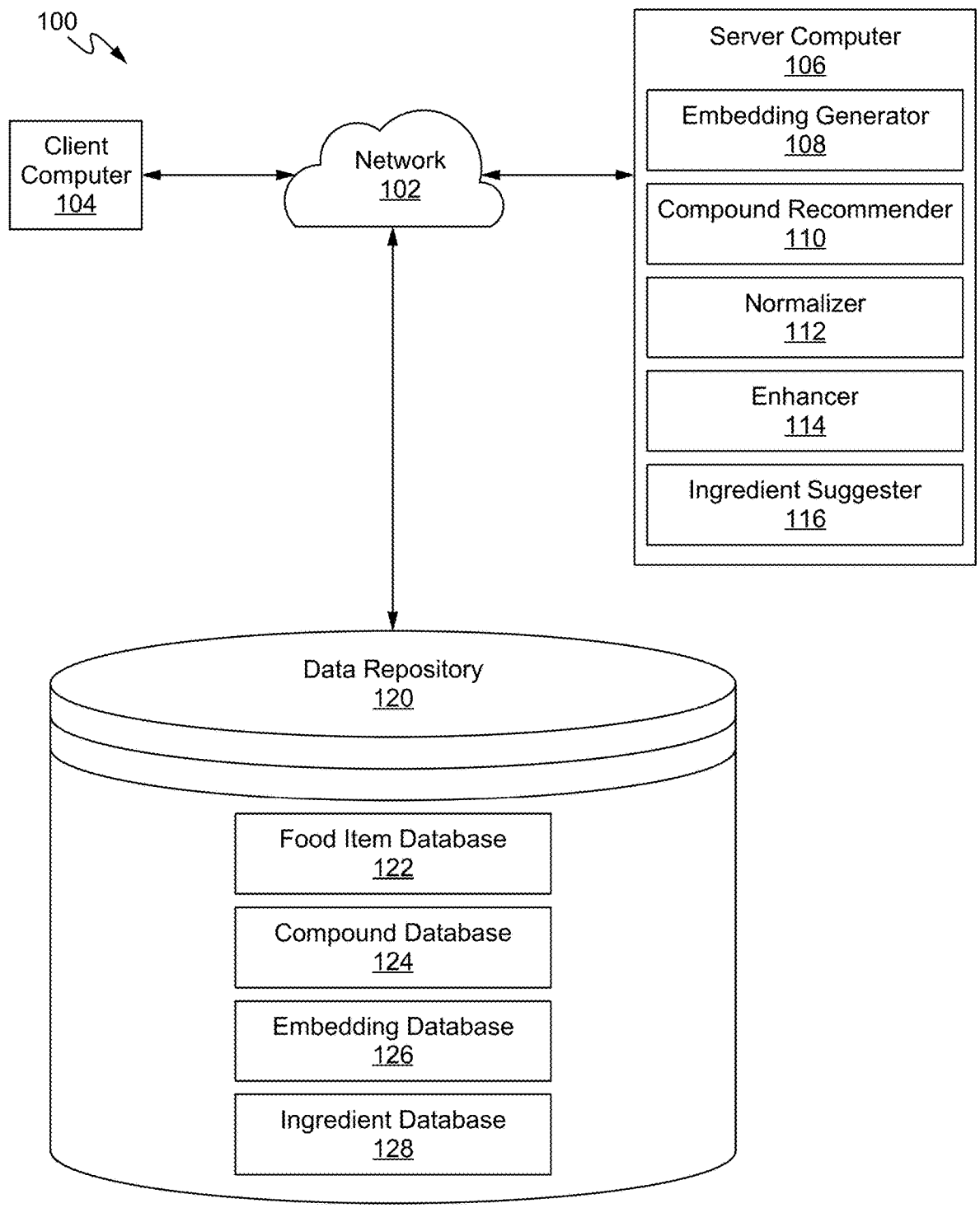
FIG. 1 illustrates an example networked computer system with which various embodiments may be practiced.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein in sections according to the following outline:

1.0 GENERAL OVERVIEW
    2.0 STRUCTURAL OVERVIEW
    3.0 FUNCTIONAL OVERVIEW
        3.1 EMBEDDING GENERATOR
            3.1.1 GRAPH MODEL
            3.1.2 WORD MODEL
            3.1.3 PROJECTION MODEL
            3.1.4 EMBEDDINGS
        3.2 COMPOUND RECOMMENDER
        3.3 NORMALIZER
        3.4 ENHANCER
        3.5 INGREDIENT SUGGESTER
    4.0 PROCEDURAL OVERVIEW
        4.1 SUGGESTING CHEMICAL COMPOUNDS
        4.2 SUGGESTING SOURCE INGREDIENTS
    5.0 HARDWARE OVERVIEW
    6.0 SOFTWARE OVERVIEW
    7.0 OTHER ASPECTS OF DISCLOSURE
    1.0 General Overview Computer-implemented techniques for generating chemical compounds with desired functional (e.g., sensorial) properties, such as flavors, odors, etc., or that may be used to recreate functional properties of target chemical compounds that are present in products, such as food items, using artificial intelligence are disclosed.

In some embodiments, an artificial intelligence model includes a graph model, a word model, and a projection model. The graph model generates compound graph embeddings for chemical compounds that are input to the artificial intelligence model. The word model generates flavor word embeddings for flavor profiles that are input to the artificial intelligence model. The projection model includes a compound projector and a flavor projector. The projection model generates a source compound projected embedding of and source flavor projected embeddings (positive and negative) for each source chemical compound by projecting a source compound graph embedding of and source flavor word embeddings (positive and negative) for each source chemical compound into the same space. During training, a loss function of the projection model is minimized such that the source compound projected embedding of a source chemical compound is aligned with its positive source flavor projected embedding but apart from its negative source flavor projected embeddings. After training, the artificial intelligence model is applied to and for at least each source chemical compound to generate source compound projected embeddings and flavor embeddings for desired flavor profiles that can be used to query for chemical compounds. To find suggested chemical compounds for a target chemical compound or a desired flavor profile, the artificial intelligence model is applied to that target chemical compound or to that desired flavor profile to generate a target chemical projected embedding or a desired flavor projected embedding. A similarity search is performed on all source compound projected embeddings or all true source flavor projected embeddings to suggest one or more source chemical using the target chemical projected embedding or the desired flavor projected embedding, depending on whether the search is for the target chemical compound or the desired flavor profile.

In an embodiment, a computer-implemented method of suggesting chemical compounds is provided. The method comprises: training an artificial intelligence model on first digital data representing a first plurality of chemical compounds, second digital data representing a first plurality of true flavor profiles of the first plurality of chemical compounds, and third digital data representing a first plurality of false flavor profiles for the first plurality of chemical compounds, wherein each chemical compound in the first plurality of chemical compounds is associated with a true flavor profile in the first plurality of true flavor profiles and with one or more false flavor profiles in the first plurality of false flavor profiles, wherein the artificial intelligence model is trained, for each chemical compound in the first plurality of chemical compounds, to align a compound projected embedding of a respective chemical compound with a positive flavor projected embedding of the true flavor profile associated with the respective chemical compound, and to distance the compound projected embedding from one or more negative flavor projected embeddings of the one or more false flavor profiles associated with the respective chemical compound; applying the trained artificial intelligence model to fourth digital data representing a second plurality of chemical compounds and a fifth digital data representing a plurality of true flavor profiles corresponding to the second plurality of chemical compounds, to generate a plurality of compound projected embeddings and a plurality of positive flavor projected embeddings, wherein each chemical compound in the second plurality of chemical compounds is associated with a compound embedding in the plurality of compound embeddings and with a positive flavor projected embedding in the plurality of positive flavor projected embeddings; receiving a request for suggested chemical compounds, wherein the request identifies a particular chemical compound or a particular flavor profile; performing a search against at least one of the plurality of compound embeddings or the plurality of positive flavor projected embeddings to determine one or more chemical compounds from the second plurality of chemical compounds that satisfy the request.

Computer-implemented techniques for suggesting sets of source ingredients that may be used to recreate functional properties of target food items are also disclosed.

In some embodiments, a computer model suggests candidate sets of source ingredients for food items that are input to the computer model. The computer model is based on solving a linear programming problem to determine a candidate set of one or more source ingredients for a target food item, in which the target food item is presented as a mixed integer programming optimization problem to be solved by the computer model. Using a matrix of chemical compound source ingredient vectors of all source ingredients, the computer model determines the candidate set of source ingredients and their corresponding quantities (amounts). The candidate ingredient set is the most optimal ingredient set for the target food item as a volatile profile for that ingredient set most closely resembles the target food item's volatile profile as compared to other ingredient sets. Objectives of the model include maximizing profile similarity between the target food item and the candidate ingredient set and minimizing profile similarity between the source ingredients in the candidate ingredient set.

In an embodiment, a computer-implemented method of suggesting source ingredients is provided. The method comprises: generating a compound concentration food item vector for each food item of a plurality of food items in a food item database, wherein the compound concentration food item vector of each food item of the plurality of food items includes, for a respective food item, first concentration data of a plurality of chemical compounds in a chemical compound database, wherein the first concentration data is based on concentration values of the plurality of chemical compound present in the respective food item; generating a compound concentration source ingredient vector for each source ingredient of a plurality of source ingredients in a source ingredient database, wherein the compound concentration source ingredient vector of each source ingredient of the plurality of source ingredients includes, for a respective source ingredient, second concentration data of the plurality of chemical compounds in the chemical compound database, wherein the second concentration data is based on concentration values of the plurality of chemical compounds present in the respective source ingredient; receiving a request that identifies a particular food item of the plurality of food items in the food item database; applying a computer model to an aggregate of compound concentration source ingredient vectors of the plurality source ingredients to generate a plurality of vectors including an ingredient quantities vector and an ingredient inclusion vector for the particular food item, wherein the ingredient inclusion vector identifies one or more source ingredients of the plurality of source ingredients to include in a candidate ingredient set and the ingredient quantities vector identifies an amount of each of the one or more source ingredients; indicating the candidate ingredient set in response to receiving the request.

All embodiments disclosed and claimed herein are directed to a computer-implemented programmed processes that interact with digital data to provide a practical application of computing technology to the problems of generating chemical compounds that have desired flavor profiles or that may be used to recreate functional (e.g., sensorial) properties, such as flavors, odors, etc., of target chemical compounds that may be expensive or can only be found from an animal source, and of suggesting sets of source ingredients that may be used to recreate functional properties of target food items. The disclosure is not intended to encompass techniques for organizing human activity, for performing mental processes, or for performing a mathematical concept, and any interpretation of the claims to encompass such techniques would be unreasonable based upon the disclosure as a whole.

Other embodiments, aspects, and features will become apparent from the reminder of the disclosure as a whole.

2.0 Structural Overview

FIG. 1 illustrates an example networked computer system 100 with which various embodiments may be practiced. FIG. 1 is shown in simplified, schematic format for purposes of illustrating a clear example and other embodiments may include more, fewer, or different elements. FIG. 1, and the other drawing figures and all of the description and claims in this disclosure, are intended to present, disclose, and claim a technical system and technical methods comprising specially programmed computers, using a special-purpose distributed computer system design and instructions that are programmed to execute the functions that are described. These elements execute functions that have not been available before to provide a practical application of computing technology to the problems of generating chemical compounds that have desired flavor profiles or that may be used to recreate functional (e.g., sensorial) properties, such as flavors, odors, etc., of target chemical compounds in food items, and of suggesting sets of source ingredients that may be used to recreate functional properties of target food items. In this manner, the disclosure presents a technical solution to a technical problem, and any interpretation of the disclosure or claims to cover any judicial exception to patent eligibility, such as an abstract idea, mental process, method of organizing human activity or mathematical algorithm, has no support in this disclosure and is erroneous.

In the example FIG. 1, the networked computer system 100 comprises a client computer(s) 104, a server computer 106, a data repository(ies) 120, which are communicatively coupled directly or indirectly via one or more networks 102. In an embodiment, the server computer 106 broadly represents one or more computers, such as one or more desktop computers, server computers, a server farm, a cloud computing platform (like Amazon EC2, Google Cloud, container orchestration (Kubernetes, Docker, etc.)), or a parallel computer, virtual computing instances in public or private datacenters, and/or instances of a server-based application.

The server computer 106 includes one or more computer programs or sequences of program instructions that is organized to implement embedding (vector) generating functions, chemical compound recommending functions, normalizing functions, enhancing functions, and ingredient suggesting functions. Programs or sequences of instructions organized to implement the embedding generating functions may be referred to herein as an embedding generator 108. Programs or sequences of instructions organized to implement the chemical compound recommending functions may be referred to herein as a compound recommender 110. Programs or sequences of instructions organized to implement the normalizing functions may be referred to herein as a normalizer 112. Programs or sequences of instructions organized to implement the ingredient enhancing functions may be referred to herein as an enhancer 114. Programs or sequences of instructions organized to implement the ingredient recommending functions may be referred to herein as an ingredient suggester 116.

In an embodiment, the embedding generator 108 is programmed to generate a chemical compound embedding for a chemical compound, a flavor embedding for a flavor profile, or both, at the same time or at different times. A chemical compound embedding is an encoded representation of the structure of a chemical compound. A flavor embedding is an encoded representation of a flavor profile, such as of a food item or for a chemical compound. A true (or false) flavor profile may include one or more true (or false) flavor descriptors describing different flavors, e.g., floral, citric, sweet, pungent, etc., of a food item or a chemical compound. The terms "descriptor," "property," and "tag" are used interchangeably herein. As further discussed below, the embedding generator 108 may be applied to source chemical compounds from a source compound database and to other chemical compounds present in food items from a food item database, and, for each chemical compound, to generate two types of chemical compound embeddings: compound graph embedding and compound projected embedding. The embedding generator 108 may be applied to true and false flavor profiles to generate, and, for each flavor profile, two types of flavor embeddings: flavor word embedding and flavor projected embedding. Flavor embeddings associated with true flavor profiles are referred to as positive flavor embeddings. Flavor embeddings associated with false flavor profiles are referred to as negative flavor embeddings.

In an embodiment, the compound recommender 110 is programmed to suggest (find, select, determine, generate, predict, recommend, etc.) one or more source chemical compounds based on a target chemical compound or based on a desired flavor profile that is indicated as input into the compound recommender 110. For example, the compound recommender 110 may suggest one or more alternative (similar) chemical compounds based on a target chemical compound (that is present in a food item) identified for replacement. Each alternative chemical compound is selected from the source compounds in the source compound database 124 and recreates functional properties of the target chemical compound.

In an embodiment, the normalizer 112 is programmed to determine normalized compound concentrations of each source ingredient in the source ingredient database 128 and each food item in the food item database 122, and to generate digital representations thereof. A digital representation is a vector including normalized concentrations of chemical compounds present in a source ingredient or a food item associated with the vector. A vector that includes normalized concentrations of chemical compounds present in a source ingredient is referred to as a normalized compound concentration source ingredient vector. A vector that includes normalized concentrations of compounds present in a food item is referred to as a normalized compound concentration food item vector.

In an embodiment, the enhancer 114 is programmed to generate enhanced compound concentration source ingredient vectors from normalized compound concentration source ingredient vectors using chemical compound descriptors or properties, such as flavors and odors. These chemical compound descriptors may be encoded in flavor embeddings of chemical compounds.

In an embodiment, the ingredient suggester 116 is programmed to suggest (find, select, determine, generate, predict, recommend, etc.) an optimal set of one or more source ingredients and corresponding quantities, based on a target food item that is indicated as input into the ingredient suggester 116. For example, the ingredient suggester 116 may suggest a candidate set of one or more source ingredients that are plant-based for an animal-based food item indicated as the input to the ingredient suggester 116. Each suggested source ingredient is selected from the source ingredients in the source ingredient database 128. The animal-based food item is a food item selected from the food item database 122 for mimicking its volatile profile. The suggested source ingredient(s) together have a volatile profile that most closely mimics the target food item's volatile profile as compared to other ingredient sets.

In some embodiments, to provide modularity and separation of function, the embedding generator 108 and the compound recommender 110 are implemented as a logically separate program, process or library.

The server computer 106 also includes receiving instructions (not illustrated) and displaying instructions (not illustrated). The receiving instructions are programmed to receive data from a client computer 104 and/or a data repository 120 for further processing. For example, the receiving instructions may be programmed for receiving user input, such as user input identifying or specifying food items, chemical compounds, flavor profiles, a number of suggested compounds to be generated, etc. The displaying instructions are programmed to cause one or more computing devices, such as a client computer 104 to display a graphical user interface (GUI) including content, such as content from data repository 120 and/or generated by the embedding generator 108, the compound recommender 110, the normalizer 112, the enhancer 114, and/or the ingredient suggester 116. Other sets of instructions may be included to form a complete system such as an operating system, utility libraries, a presentation layer, database interface layer and so forth.

Computer executable instructions described herein may be in machine executable code in the instruction set of a CPU and may have been compiled based upon source code written in Python, JAVA, C, C++, OBJECTIVE-C, or any other human-readable programming language or environment, alone or in combination with scripts in JAVASCRIPT, other scripting languages and other programming source text. In another embodiment, the programmed instructions also may represent one or more files or projects of source code that are digitally stored in a mass storage device such as non-volatile RAM or disk storage, in the systems of FIG. 1 or a separate repository system, which when compiled or interpreted cause generating executable instructions which when executed cause the computer to perform the functions or operations that are described herein with reference to those instructions. In other words, the figure may represent the manner in which programmers or software developers organize and arrange source code for later compilation into an executable, or interpretation into bytecode or the equivalent, for execution by the server computer 106.

The server computer 106 may be coupled, indirectly or directly, to the data repository 120 that includes a food item database 122, a source compound database 124, an embedding database 126, a source ingredient database 128. As used herein, the term "database" refers to a corpus of data, organized or unorganized, in any format, with or without a particular interface for accessing the corpus of data. Each database 122, 124, 126, 128 may be implemented using memory, e.g., RAM, EEPROM, flash memory, hard disk drives, optical disc drives, solid state memory, or any type of memory suitable for database storage.

The food item database 122 includes a plurality of food items and information about the plurality of food item. A food item in the food item database 122 may be plant-based or animal-based. An example plant-based food item is tofu. An example animal-based food item is pulled pork.

Each food item in the food item database 122 is associated with gas chromatography mass spectrometry (GCMS) data obtained using GCMS techniques. GCMS techniques may be used to perform a GCMS analysis on a food item to determine the molecular composition of the food item. GCMS data may include one or more readouts, with each of the one or more readouts including a list of chemical compounds of the food item. For example, a first readout may include a human-verified list of chemical compounds, and a second readout may include a software-produced list of chemical compounds.

In an embodiment, the human-verified list of chemical compounds for the food item may include compound data, odor threshold data, and concentration data. The human-verified list of chemical compounds may stem from a predetermined list of chemical compounds with known odor thresholds. An odor threshold represents the lowest concentration of a chemical compound required for a human to be able to detect it within a solution, such as water with parts per billion as the unit. (It is noted that odors are relevant when creating a flavor. Studies suggest that odor is the dominant role in our experience of food.) A lab technician may check the existence of each chemical compound from the predetermined list by analyzing the retention time of the chemical compound and the presence of its ions within the corresponding GCMS spectrum, and may determine the concentration of each of those chemical compounds in the food item by comparing it with the spectrum of an added baseline sample.

In an embodiment, the software-produced list of chemical compounds for the food item may include compound data, concentration data, and confidence data. The chemical compound data and concentration data in the software-produced list are similarly configured as the chemical compound data and concentration data in the human-verified list, in that the chemical compound data includes chemical compounds that are present in the food item and the concentration data includes the concentration of each of those chemical compounds that are present in the food item. The confidence data in the software-produced list includes a score for each chemical compound indicating the likelihood of that chemical compound being present in the food item. The chemical compounds are automatically found by a GCMS software.

The readouts from the GCMS analysis are combined into a chemical compound list for the food item, with chemical compounds from the first readout (e.g., human-verified list of compounds) weighted higher than chemical compounds from the second readout (e.g., software produced list of compounds) as odor thresholds of the chemical compounds from the second readout may be unknown and/or the confidence may be lower. The chemical compound list also includes the concentration of each of the chemical compounds in the list.

In an embodiment, the chemical compound list is presented, for example, in a GUI, to a user to select therefrom a target chemical compound for replacement during a chemical compound suggestion process. In an embodiment, each chemical compound in the list may be ranked by its ratio between odor threshold and concentration of that chemical compound. As such, since the second readout is not associated with odor thresholds, and as such the importance of each chemical compound from the second readout is unknown, chemical compounds from the second readout are ranked lower than chemical compounds from the first readout and are at the end of the combined compound list.

Each chemical compound in the combined compound list may be associated with a simplified molecular-input line-entry system (SMILES) based notation describing its corresponding structure, although other suitable notations that allow for chemical information processing are also contemplated. For example, the chemical compound structure of vanillin may be represented as O=Cc1ccc(O)c(OC)c1COc1cc(C=O)ccc1O.

The combined compound list associated with each food item is stored in the food item database 122.

Each food item in the food item database 122 may also be associated with a volatile profile that includes all relevant volatile molecules present in the food item. These volatile molecules and their corresponding concentrations may be determined from the GCMS data for the food item. In an embodiment, the volatile profile of each food item in the food database 122 may include normalized concentration data which includes, for the relevant molecules, compound concentration values (e.g., concentration data) normalized by odor threshold values (e.g., odor threshold data). The volatile profile of each food item in the food item database 122 is digitally represented as a normalized compound concentration food item vector.

Each food item in the food item database 122 may also be associated with a corresponding flavor profile that includes one or more flavor descriptors describing the flavors of the food item. A flavor profile may be determined using a classification method described in co-pending U.S. patent application Ser. No. 17/221,129, filed Apr. 2, 2021, titled "Method of Classifying Flavors," wherein the entire contents of which are hereby incorporated by reference as if fully set forth herein. For example, a flavor generator may include a certainty level classifier that generates, for each flavor category of a plurality of flavor categories, a certainty level to indicate a level of certainty that a flavor associated with that flavor category is present. The flavor generator may also include a plurality of flavor predictors associated with the plurality of flavor categories. Each flavor predictor generates a deeper level of flavor granularity corresponding to an associated flavor category. Alternatively, a flavor profile may be obtained using different methods or techniques. For example, a flavor profile may be obtained from one or more of different sources of knowledge, including open-source databases such as the FlavorDB database, the FooDB database, the Good Scents Company database, or the like.

Table 1 shows example information associated with each food item stored in the food item database 122.

TABLE 1

| Food Item Information | Description |
| --- | --- |
| Formula | Ingredients and corresponding amounts, weights, proportions, etc. |
| Databases | Database identifier in various databases (web sources) |
| Compounds | Readings from GCMS analysis |
| Flavors | Tags, descriptions, type |

In an embodiment, food items in the food item database 122 are presented, for example, in a GUI, to a user to select therefrom a target food item for mimicking its volatile profile during a source ingredient suggestion process.

The source compound database 124 includes a plurality of source chemical compounds and information about the plurality of source chemical compounds, including structural and organoleptic (e.g., flavors, odors, etc.) information. The source compound database 124 also includes associations between the plurality of source chemical compounds and ingredients that contain them. In an embodiment, the ingredients associated with the plurality of source chemical compounds are natural ingredients. Associations with natural ingredients are useful for multiple reasons. First, using natural ingredients rather than flavorings are preferable for consumer transparency and provides potential for novel ingredient combinations. Secondly, compounds used in flavorings must be able to be extracted from natural ingredients to be considered a "Natural Flavor." Therefore, associations with natural ingredients can help flavorists select potential natural sources from which to extract flavorings. In an embodiment, the ingredients associated with the plurality of source chemical compounds are plant-based ingredients.

In an embodiment, data in the source compound database 124 may be obtained from one or more different sources of knowledge, including open-source databases such as the FlavorDB database, the FooDB database, the Good Scents Company database, or the like. Table 2 shows example information associated with each source chemical compound stored in the source compound database 124.

TABLE 2

| Compound Information | Description |
| --- | --- |
| Properties | Structural information, class, category |
| Databases | Database identifier in various databases (web sources) |
| Synonyms | Set of synonyms |
| Flavors | Tags, descriptions, type |
| Odors | Tags, descriptions, type, strength, substantivity |
| Ingredients | Natural ingredients the chemical compound is found in |

The source chemical compound may be compounds certified by the Flavor & Extract Manufacturers Association (FEMA) and, as such, may be used by flavor houses to recreate flavors, as these source chemical compounds are certified GRAS (generally regarded as safe). Each source chemical compound in the source compound database 124 may be associated with a SMILES based notation describing its corresponding structure, although other suitable notations that allow for chemical information processing are also contemplated.

A training dataset, for training the embedding generator 108, includes compound structures and corresponding flavor profiles, that each includes one or more flavor descriptors, for at least a subset of the source chemical compounds from the source compound database 124. As further discussed below, a source chemical compound in the training set is associated with a flavor profile of the actual or true flavor of the chemical compound and with one or more flavor profiles of false flavors for the chemical compound.

In an embodiment, the embedding database 126 includes compound embeddings and flavor embeddings generated by the embedding generator 108. Compound embeddings include compound graph embeddings and compound projected embeddings. The compound graph embeddings and compound projected embeddings include at least source compound graph embeddings and source compound projected embeddings associated with source chemical compounds in the training dataset. Flavor embeddings include flavor word embeddings and flavor projected embeddings. The flavor word embeddings and flavor projected embeddings include at least source flavor word embeddings and source flavor projected embeddings associated with flavor profiles of source chemical compounds in the training dataset. In an embodiment, the flavor embeddings are not stored in the embedding database 126 but are rather generated dynamically.

The source compound projected embeddings, corresponding with the source chemical compounds in the training dataset, are used by the compound recommender 110 to suggest one or more alternative (similar) chemical compounds, which are selected from the source chemical compounds in the source compound database 124, based on a target compound projected embedding as input into the compound recommender 110. Similarly, the positive source flavor projected embeddings, corresponding with the source chemical compounds in the training dataset, are used by the compound recommender 110 to suggest one or more chemical compounds, which are selected from the source chemical compounds in the source compound database 124, based on a desired flavor projected embedding as input into the compound recommender 110. For example, a positive flavor projected embedding, corresponding to the desired flavor profile, is dynamically generated and subsequent used by the compound recommender 110 to suggest one or more chemical compounds, which are selected from the source chemical compounds in the source compound database 124, based on the desired flavor projected embedding (e.g., the positive flavor projected embedding) as input into the compound recommender 110. Embeddings are further discussed below.

The source ingredient database 128 includes ingredients that are identified as natural ingredients by various sources, such as from USDA's National Agricultural Library. A natural ingredient may be plant-based, animal-based, or a combination thereof. Some non-limiting examples of plant-based ingredients may include vegetables (e.g., onions, potatoes, garlic, spinach, carrots, celery, squash, etc.), fruits (e.g., apples, pears, grapes, etc.), herbs (e.g., oregano, cilantro, basil, etc.), spices (e.g., black peppers, turmeric, red chili peppers, cinnamon, etc.), oils (e.g., corn oil, olive oil, etc.), nuts (e.g., almonds, walnuts, pistachios, etc.), legumes (e.g., lentils, dried peas, soybeans, etc.), starch, proteins, fibers, carbohydrates, sugar, etc. Some non-limiting examples of animal-based ingredients may include milk, eggs, meat products (e.g., chicken, pork, beef, etc.), and/or seafood (e.g., fish, crab, lobsters, etc.). In an embodiment, the source ingredient database 128 only includes source ingredients that are natural.

In an embodiment, each source ingredient in the source ingredient database 128 is associated with gas chromatography mass spectrometry (GCMS) data obtained using GCMS techniques. Similar to GCMS data for a food item, GCMS data for a source ingredient may include one or more readouts, with each of the one or more readouts including a list of chemical compounds of the source ingredient, and the readouts from the GCMS analysis are combined into a chemical compound list for the source ingredient. The combined compound list associated with each source ingredient is stored in the source ingredient database 128.

Each source ingredient in the source ingredient database 128 may also be associated with a volatile profile that includes all relevant volatile molecules present in the source ingredient. These volatile molecules and their corresponding concentrations may be determined from the GCMS data for the source ingredient. In an embodiment, the volatile profile of each source ingredient in the source ingredient database 128 may include normalized concentration data which includes, for the relevant volatile molecules, compound concentration values (e.g., concentration data) normalized by odor threshold values (e.g., odor threshold data). The volatile profile of each source ingredient in the source ingredient database 128 is digitally represented as a normalized compound concentration source ingredient vector, which may be enhanced using chemical compound descriptors or properties, such as flavor and odor, to obtain an enhanced compound concentration source ingredient vector.

The network 102 broadly represents a combination of one or more local area networks (LANs), wide area networks (WANs), metropolitan area networks (MANs), global interconnected internetworks, such as the public internet, or a combination thereof. Each such network may use or execute stored programs that implement internetworking protocols according to standards such as the Open Systems Interconnect (OSI) multi-layer networking model, including but not limited to Transmission Control Protocol (TCP) or User Datagram Protocol (UDP), Internet Protocol (IP), Hypertext Transfer Protocol (HTTP), and so forth. All computers described herein may be configured to connect to the network 102 and the disclosure presumes that all elements of FIG. 1 are communicatively coupled via the network 102. The various elements depicted in FIG. 1 may also communicate with each other via direct communications links that are not depicted in FIG. 1 for purposes of explanation.

The server computer 106 is accessible over the network 102 by a client computer 104 to request alternative chemical compounds for a particular chemical compound, to request chemical compounds for a desired flavor profile, and/or to request a set of source ingredients for a target food item. The client computer 104 may comprise a desktop computer, laptop computer, tablet computer, smartphone, or any other type of computing device that allows access to the server computer 106. The elements in FIG. 1 are intended to represent one workable embodiment but are not intended to constrain or limit the number of elements that could be used in other embodiments.

3.0 Functional Overview

The server computer 106, including the embedding generator 108, the compound recommender 110, the normalizer 112, the enhancer 114, and the ingredient suggester 116, and the data repository 120 interoperate programmatically in an unconventional manner, depending on use requirements, to suggest alternative chemical compounds for (based on) a target chemical compound, to suggest chemical compounds for (based on) a desired flavor profile, and/or suggest ingredients for (based on) a target food item.

For example, the embedding generator 108, the compound recommender 110, and/or the data repository 120 interoperate programmatically in an unconventional manner to suggest alternative chemical compounds for (based on) a target chemical compound that is present a food item for replacement and to recreate functional properties of that target chemical compound.

For another example, the embedding generator 108, the compound recommender 110, and/or the data repository 120 interoperate programmatically in an unconventional manner to suggest chemical compounds for (based on) for a desired flavor profile.

For yet another example, the embedding generator 108, the normalizer 112, the enhancer 114, the ingredient suggester 116, and/or the data repository 120 interoperate programmatically in an unconventional manner to suggest source ingredients for (based on) a target food item.

3.1 Embedding Generator

Figure 2:
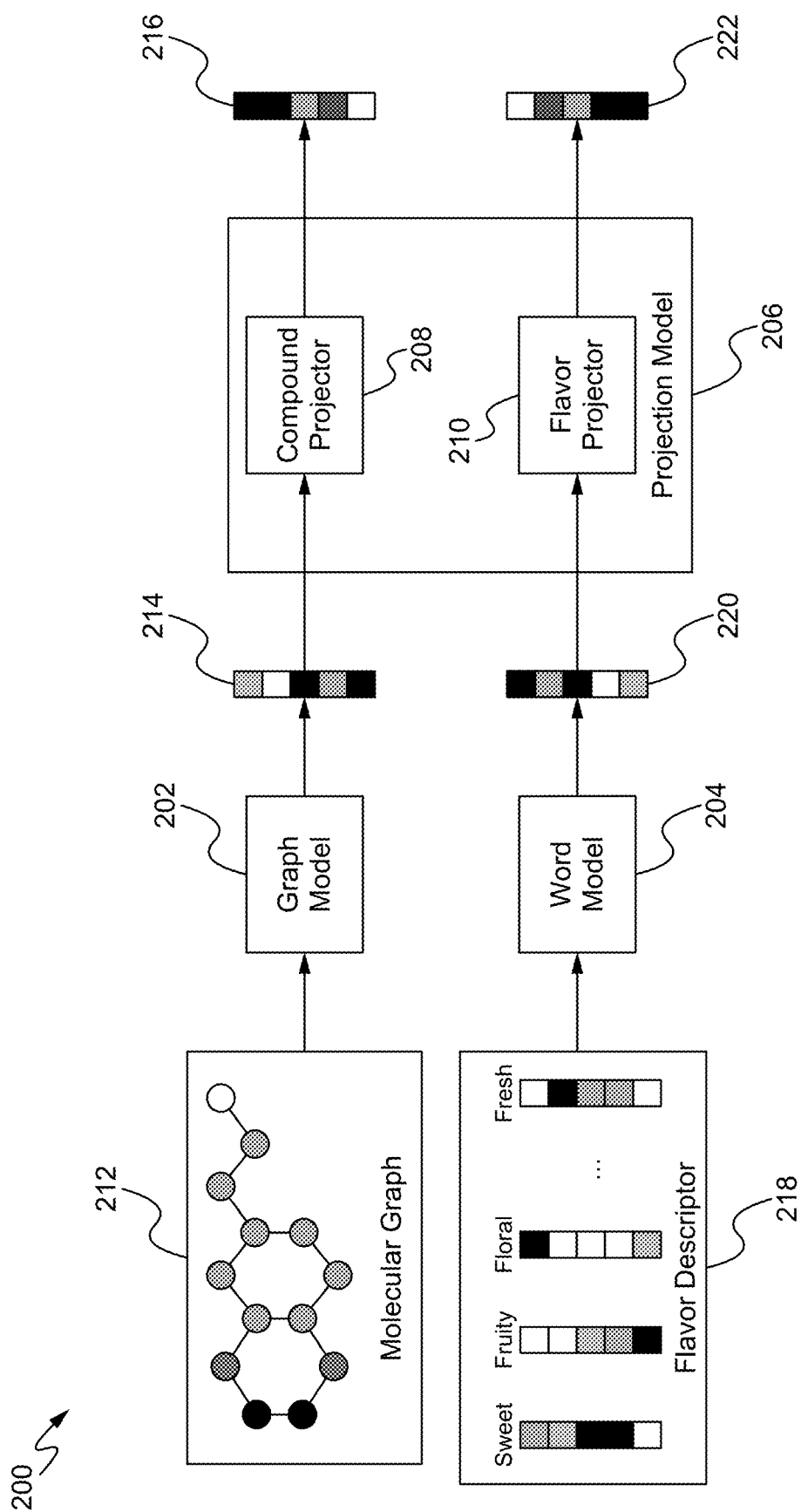
FIG. 2 illustrates an architecture of an example artificial intelligence model, in accordance with some embodiments.

In an embodiment, the embedding generator 108 includes an artificial intelligence model that is trained to learn relationships between chemical compounds and their known flavor profiles. Once the embedding generator 108 is trained, the embedding generator 108 is able to generate representations (embeddings) of unseen or new chemical compounds (e.g., chemical compounds with unknown flavors) and of new flavor profiles. FIG. 2 illustrates the architecture of artificial intelligence model 200, in accordance with some embodiments. The training dataset for training the artificial intelligence model 200 includes compound structures and associated known flavor profiles of at least a subset of source chemical compounds from the source compound database 124.

The artificial intelligence model 200 of FIG. 2 includes three parts: a graph model 202, a word model 204, and a projection model 206. The projection model 206 includes two projectors: a compound projector 208 and a flavor projector 210. Each of the compound projector 208 and the flavor projector 210 is based on a neural network architecture. By training the artificial intelligence model 200, layers of the projection model 206 (specifically, of the compound projector 208 and the flavor projector 210) will contain information pertaining to compound structures and associated flavors. As further described below, this information is useful for a variety of tasks, such as finding alternative (similar) chemical compounds for a target chemical compound or finding chemical compounds with a desired flavor profile.

3.1.1 Graph Model

The graph model 202 may be based on a graph neural network, such as a graph convolution network, a graph isomorphism network, a graph attention network, or the like.

During training, a notation suitable for processing, such as the SMILES notation, of the molecular structure of each molecule (chemical compound) 212 from the training dataset is transformed into a graph. A graph is a data structure comprising nodes and edges connected together to represent information. Each node in the graph represents an atom in the molecule. Each of the nodes in the graph is initialized with a set of one or more features defining an atom, such as atomic weight, valence, and hybridization type, that corresponds with the node. The features may be obtained from an open-source cheminformatics software package, such as RDKit, that contains basic information about atoms and chemical compounds. An edge between two nodes in the graph represent a bond between the atoms corresponding with the nodes.

In an embodiment, the graph model 202 operates on the graph after the nodes in the graph are initialized. The graph network 202 performs message passing (neighborhood aggregation) between the nodes. Message passing involves pushing weights from each node to neighboring nodes that are connected via edges to that node, thus updating the internal representation for that node. Message passing is performed, in parallel, on all nodes in the graph, as information in layer M+1 depend on information in layer M. Through N iterations (e.g., N=5), the nodes know more about their own features and that of their neighboring nodes, which creates a more accurate or fuller representation of the graph (e.g., each node has more information about its neighboring nodes), where N is a hyperparameter. At the end of the message passing, each node will have a representation that is informed by the structure of the molecule.

After N iterations, a representation of the graph is an input to the projection model 206. A computation on all node representations is performed to obtain a compound graph embedding 214 that represents the graph. In an embodiment, the mean of all node representations is calculated as the output of the graph model 202, which is input to the projection model 206.

3.1.2 Word Model

The word model 204 includes a language-based model such as Bidirectional Encoder Representation from Transformers (BERT), Enhanced Language Representation with Informative Entities (ERNIE), Generative Pre-Trained Transformer (GPT), or the like. The word model 204 receives a flavor profile as input and transforms flavor descriptors of the flavor profile to vectors by using the language-based model. The word model 204 then combines the vectors into a single flavor word embedding 220 using a combination technique, such as averaging, inverse of occurrence in dataset, attention, or the like. The flavor word embedding 220, output from the word model 204, is input to the projection model 206.

A flavor profile for a chemical compound in the training set may be of the actual or true flavor or of a false flavor for the chemical compound. The true flavor profile describes the actual flavor of the chemical compound. A false flavor profile describes a false flavor of a negative example in which the false flavor is different from the chemical compound's actual flavor. Negative examples may be sampled or generated using different techniques. One technique is using a flavor profile from a different compound. Another technique is to replace one or more flavor descriptors for other flavor descriptors and computing the corresponding flavor word embedding and, in turn, the corresponding flavor projected embedding. While there is only one true flavor profile associated with a chemical compound, there may be many false flavor profiles associated with the chemical compound. In an embodiment, false flavor profiles associated with the chemical compound may be generated prior to or during training of any one or more models described herein.

3.1.3 Projection Model

As described herein, the projection model 206 learns relationships between chemical compounds and its flavors (true and false flavors). The projection model 206 includes the compound projector 208 and the flavor projector 210. In an embodiment, each of the compound projector 208 and the flavor projector 210 includes a projection layer. The projection layer may be a linear layer or a linear feed-forward layer. An example function of projection layer of compound projector 208 is $g_{out}=w_g g_{in}+b_g$, where $g_{in}$ is the compound graph embedding 214 that is output from the graph model 202, $w_g$ and $b_g$ are the respective weight and bias values of the graph, and $g_{out}$ is the compound projected embedding. Similarly, an example function of projection layer of the flavor projector 208 is $f_{out}=w_f f_{in}+b_f$, where $f_{in}$ is the flavor word embedding 220 that is output from the word model 204, $w_f$ and $b_f$ are the respective weight and bias values of the flavor, and $f_{out}$ is the flavor projected embedding.

The projection model 206 is trained to project both the compound graph embedding 216 and positive and negative flavor word embeddings 222 of a chemical compound into a common or joint space in a particular manner described below and to/by minimizing a loss function L of the projection model 206.

In an embodiment, the loss function L of the projection model 206 is a combination of semantic loss $L_{sem}$ and similarity loss $L_{sim}$. The semantic loss $L_{sem}$ looks to preserve the information of the chemical compound graph. The similarly loss $L_{sim}$ uses the TripletLoss function to bring the graph projected embedding and the positive flavor projected embedding closer. The loss function L is $L_{sim}+\lambda L_{sem}$, where $L_{sem}=\mathcal{L}_{sem}(p, r)$ and $L_{sim}=\text{TripletLoss}(g_{out}, f_{out}, n_{out})$.

More specifically, the objective of the semantic loss $L_{sem}$ is to ensure that the graph projected embedding 216 contains structural information that was originally in the chemical compound graph. For example, the projection model 206 predicts what the chemical compound's weight is (where r represents the chemical compounds weight, and p represents the prediction by the projection model 206). In essence, the semantic loss $L_{sem}$ forces the projection model 206 to preserve the graph's information, which in turn is used to learn the relationship between the structure of the graph and the flavor.

The TripletLoss function learns a distributed embedding by the notion of similarity and dissimilarity. The TripletLoss function aligns an anchor input (e.g., compound projected embedding) to a positive input (e.g., true flavor) and makes the anchor far from a negative input (e.g., false flavor). By comparing the graph projected embedding with its positive flavor projected embedding (true flavor) and one or more negative flavor projected embeddings (false flavors), the loss function L makes to make the graph projected embedding get closer to its positive flavor projected embedding and further from the negative projected embeddings.

The value of the loss function L indicates how well the projection model 206 is doing. In an embodiment, the learning algorithm of the projection model 206 may be a semi-supervised learning algorithm or an unsupervised learning algorithm. For example, as described above, the training data includes compound projected embeddings and their known flavor projected embeddings (positive and negative) of at least a subset of source chemical compounds from the source compound database 124. A compound projected embedding is aligned with its positive flavor projected embedding and away from negative flavor projected embeddings. The projection model 206 is trained by re-adjusting parameters (e.g., sets of weight and bias values) of the compound projector 208 and the flavor projector 210 to minimize the loss function L.

Other projection techniques, such as a multi-layer perceptron (MLP) neural network, are contemplated and may be used to project a compound graph embedding and flavor word embeddings associated with a chemical compound into a common or joint space.

3.1.4 Embeddings

After the embedding generator 108 or, in an embodiment, after the projection model 206 is trained, the embedding generator 108 is applied to at least each of the source chemical compounds in the training dataset and their associated true flavor profiles. In an embodiment, the embedding generator 108 is applied to all source chemical compounds in the compound database 124 and their associated true flavor profiles. Source compound projected embeddings may be retrieved or extracted from the compound projection layer of the projection model 206 (more specifically, of the compound projector 208). Source flavor projected embeddings may be retrieved or extracted from the flavor projection layer of the projection model 206 (more specifically, of the flavor projector 210). The source compound projected embeddings and at least the positive source flavor projected embeddings corresponding with the source chemical compounds in the training dataset are associated and stored in the embedding database 126.

The embedding generator 108 may also be applied to a target chemical compound, for example, of a food item (in the food item database 122) that is to be replaced. The target chemical compound may be selected from a combined compound list for the food item. A target compound projected embedding, corresponding to the target chemical compound of the food item, from the compound projection layer is retrieved (extracted) and may be stored in the embedding database 126.

Similarly, the embedding generator 108 may be applied to a desired flavor profile of a food item or chemical compound. A desired flavor projected embedding, corresponding to the desired flavor profile, from the flavor projection layer is retrieved (extracted) and may be stored in the embedding database 126.

3.2 Compound Recommender

To find or suggest chemical compounds that may be used to recreate flavors, the compound recommender 110 searches all source compound projected embeddings, of source chemical compounds, in the embedding database 126 to find top-K chemical compounds that are similar (closest) to the target compound projected embedding of a target chemical compound in the common space, using a similarly search. Likewise, to find or suggest chemical compounds that have flavor profiles that match a desired flavor profile, the compound recommender 110 searches all positive flavor projected embeddings, of source chemical compounds, in the embedding database 126 to find top-K chemical compounds that have positive source flavor projected embeddings that are similar (closest) to the desired flavor in the common space projected embedding of a desired flavor profile, using a similarly search.

Example similar search is a cosine similarity search, a Euclidean similarity search, or a FAISS vector similarity search. For example, using a similarity search, each of the top-K chemical compounds suggested is similar to the target chemical compound with regards to structural and functional features. This is useful if the target compound in the food item is expensive or can only be found from an animal source.

After suggesting source chemical compounds, the compound recommender 110 may suggest plant-based ingredients that contain the suggested source chemical compounds by referencing the source compound database 124. In an embodiment, the suggested source chemical compounds and/or corresponding plant-based ingredients may be returned as a result.

3.3 Normalizer

In an embodiment, the normalizer 112 generates normalized compound concentration data for each input to the normalizer 112. An input to the normalizer 112 may be a source ingredient or a food item. The normalizer 112 uses GCMS data of the input to generate normalized compound concentration data. The normalizer 112 uses the GCMS data to determine the volatile molecules and their corresponding concentration values and odor threshold values, and normalizes the compound concentration values by their respective odor threshold values. The odor threshold value for a chemical compound is the concentration of the chemical compound in water/lipid solution needed for a human to be able to perceive it. The normalized compound concentration data includes the compound concentration values (e.g., concentration data) normalized by odor threshold values (e.g., odor threshold data) for all volatile molecules.

Using these techniques, the normalizer 112 generates normalized compound concentration data for each source ingredient in the source ingredient database 128 and for each food item in the food item database 122.

Normalized compound concentration data for a source ingredient or a food item is included in the volatile profile of that source ingredient or food item. Normalized concentration data may be visualized or rendered on a GUI as graphs and/or charts. Normalized concentration data of each source ingredient in the source ingredient database 128 may be digitally represented as a normalized compound concentration source ingredient vector. Normalized concentration data of each food item in the food item database 122 may be digitally represented as a normalized compound concentration food item vector. Normalized compound concentration source ingredient vectors and normalized compound concentration food item vectors are used by the ingredient suggester 116 to suggest optimal sets of one or more ingredients that have volatile profiles most similar to those of target food items (e.g., food items selected from the food item database 122 for mimicking corresponding volatile profiles).

3.4 Enhancer

In an embodiment, the enhancer 114 generates enhanced compound concentration data for each input to the enhancer 114. An input to the enhancer 114 is a source ingredient. The enhanced compound concentration data includes properties of the source ingredient's flavor or odor.

The enhancer 114 may use molecular properties, which are encoded in flavor word embeddings or flavor projected embeddings of chemical compounds generated by the embedding generator 108, to provide more information of the source ingredient. In this manner, properties of the source ingredient's flavor or odor may be inferred. For example, an enhanced compound concentration source ingredient vector for the source ingredient may be generated from functional properties of chemical compounds in the source ingredient (e.g., flavor embeddings) and from each chemical compound's concentration (normalized compound concentration ingredient vectors).

Enhanced compound concentration source ingredient vectors, rather than normalized compound concentration source ingredient vectors, may be used by the ingredient suggester 116 to suggest a candidate set of one or more ingredients that will create a volatile profile similar to that of a target food item. In essence, the volatile profile of the candidate set of one or more ingredients is the optimal ingredient set as it best resembles the volatile profile of the target food item than other ingredient sets.

3.5 Ingredient Suggester

In an embodiment, the ingredient suggester 116 includes a computer model based on solving a linear programming problem. The ingredient suggester 116 suggests an optimal set of one or more source ingredients that has a volatile profile that best mimics (resembles, similar to, etc.) that of a target food item. Each target food item may be a mixed integer programming optimization problem. The most relevant source ingredients and their corresponding quantities are determined solving the optimization problem.

In use, the ingredient suggester 116 uses an aggregation (matrix) of compound concentration source ingredient vectors of all source ingredients in the source ingredient database 128. The compound concentration source ingredient vectors may be normalized compound concentration vectors, which are based on the volatile profiles of the source ingredients. Alternatively, the compound concentration source ingredient vectors may be enhanced compound concentration vectors, which are normalized compound concentration vectors enhanced with molecular properties, such as flavor and odor. In use, the ingredient suggester 116 also uses one or more compound concentration food item vectors of food items in the food item database 122. All concentration vectors are the same length, which is equal to the total number of chemical compounds in the source compound database 124. If a source ingredient or a food item does not contain a specific chemical compound, it is assigned a concentration of zero.

Ingredient suggestions and quantities are determined by solving the optimization problem. The ingredient suggester 116 determines a source ingredient inclusion vector/and a source ingredient quantities vector Q. Vector I indicates which source ingredients to include and vector Q indicates how much of each source ingredient to include such that a corresponding volatile profile is similar to that of the target food item. Profile similarity between the target food item and the source ingredients in the optimal set is maximized (e.g., volatile profile of the optimal set best mimics the volatile profile of the target food item), which is an objective function of the model, while profile similarity between the source ingredients in the optimal set is minimized (e.g., different source ingredients are selected), which is another objective function of the model. In an embodiment, the model imposes a restriction on the quantities of source ingredients such that impossibly large or small quantities of ingredients are avoided. In an embodiment, the model imposes a restriction on the maximum number of source ingredients such that the number of source ingredients is not unrealistically high.

By multiplying matrix V (which is an aggregation of the compound concentration source ingredient vectors of all source ingredients) by vector Q (which is the source ingredients quantities vector) by vector I (which is the ingredient inclusion vector), the volatile profile for the combination of source ingredients is generated.

4.0 Procedural Overview 4.1 Suggesting Chemical Compounds

Figure 3:
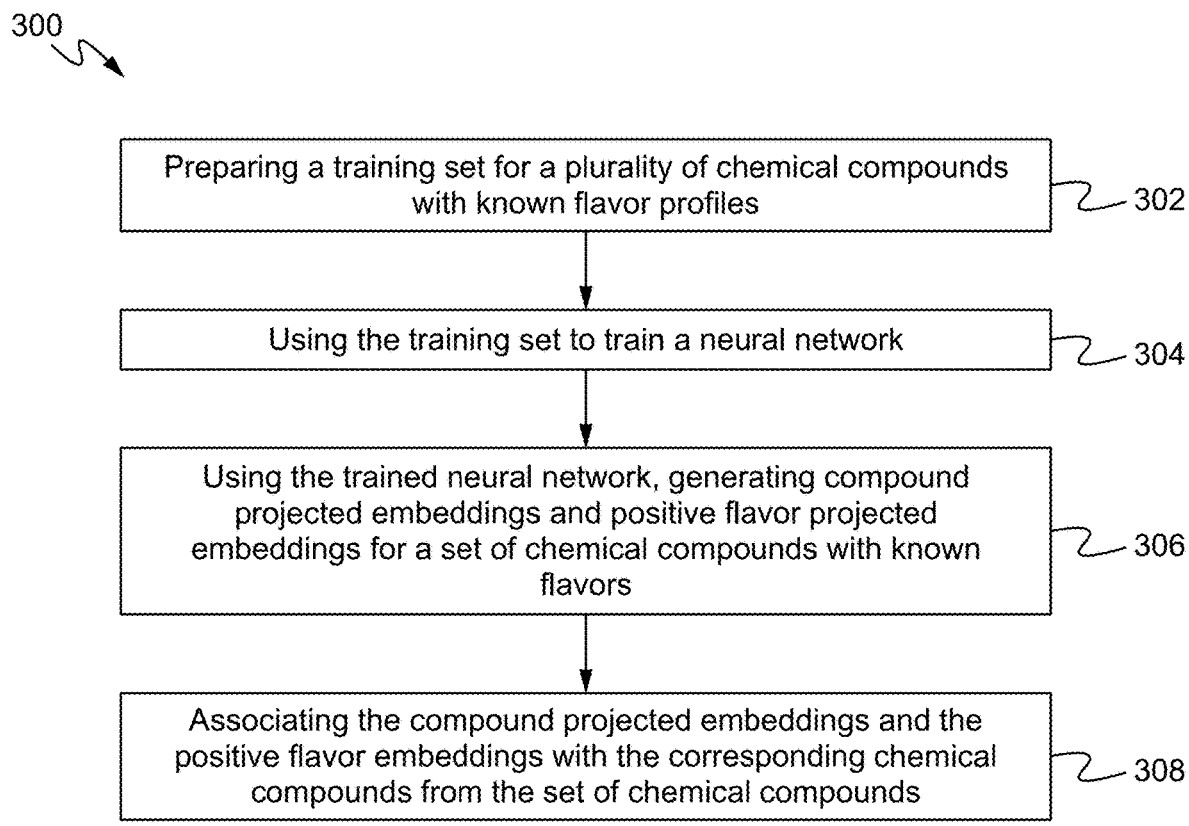
FIG. 3 illustrates an example method to generate projected embeddings for chemical compounds, in accordance with some embodiments.

FIG. 3 illustrates an example method to generate projected embeddings for chemical compounds, in accordance with some embodiments. FIG. 3 may be used as a basis to code the method 300 as one or more computer programs or other software elements that a server computer can execute or host.

At step 302, a training set for a plurality of chemical compounds with known flavor profiles is prepared for training a neural network model. For example, the plurality of chemical compounds is from the compound database 124. The plurality of chemical compounds may be a subset of or may include all source compounds in the compound database 124. The training set includes a compound graph embedding and flavor word embeddings corresponding to each chemical compound in the plurality of chemical compounds.

In an embodiment, the compound graph embedding is determined by the graph model 202. The graph model 202 transforms the molecular structure of the chemical compound into a graph and generates the compound graph embedding, which is representative of the graph. In an embodiment, flavor word embeddings for the chemical compound are determined by a word model 204. The word model 204 generates a single flavor word embedding representative of a flavor profile, which may be a true flavor profile of or may be a false flavor profile for the chemical compound. One or more false flavor profiles may be generated at step 302. The flavor word embeddings include the positive flavor word embedding of the chemical compound and at least one negative flavor word embedding for the chemical compound.

At step 304, the neural network model is trained using the training set. For example, the neural network model is the projection model 206, which receives the compound graph embedding of and the flavor word embeddings (positive and negative) for the chemical compound in the training set and projects them into a common or joint space. The compound graph embedding is projected using the compound projector 208, which generates a compound projected embedding that can be extracted from the projection layer of the compound projector 208. The flavor word embeddings are projected using the flavor projector 210, which generates flavor projected embeddings (positive and negative) that can be extracted from the projection layer of the flavor projector 210. The projection model 206 is trained to align both the compound projected embedding and the positive flavor projected embedding and to distance the compound projected embedding from the negative flavor projected embeddings.

At step 306, using the trained neural network model, compound projected embeddings and positive flavor projected embeddings for a set of chemical compounds with known flavor profiles are generated. For example, the embedding generator 108 are applied to compound graph embeddings and positive flavor word embeddings for the set of chemical compounds. In an embodiment, the set of chemical compounds with known flavor profiles includes at least those chemical compounds in the training set.

At step 308, the compound projected embeddings and the positive flavor embeddings are associated with their corresponding chemical compounds from the set of chemical compounds and are stored in a data repository for a variety of subsequent tasks. For example, the compound projected embeddings and the positive flavor embeddings may be stored in the embedding database 126 and may be used by the compound recommender 110 to find alternative (similar) chemical compounds to recreate functional properties of a target chemical compound (e.g., substitute chemical compounds for the target chemical compound) or find chemical compounds with a desired flavor profile.

Figure 4:
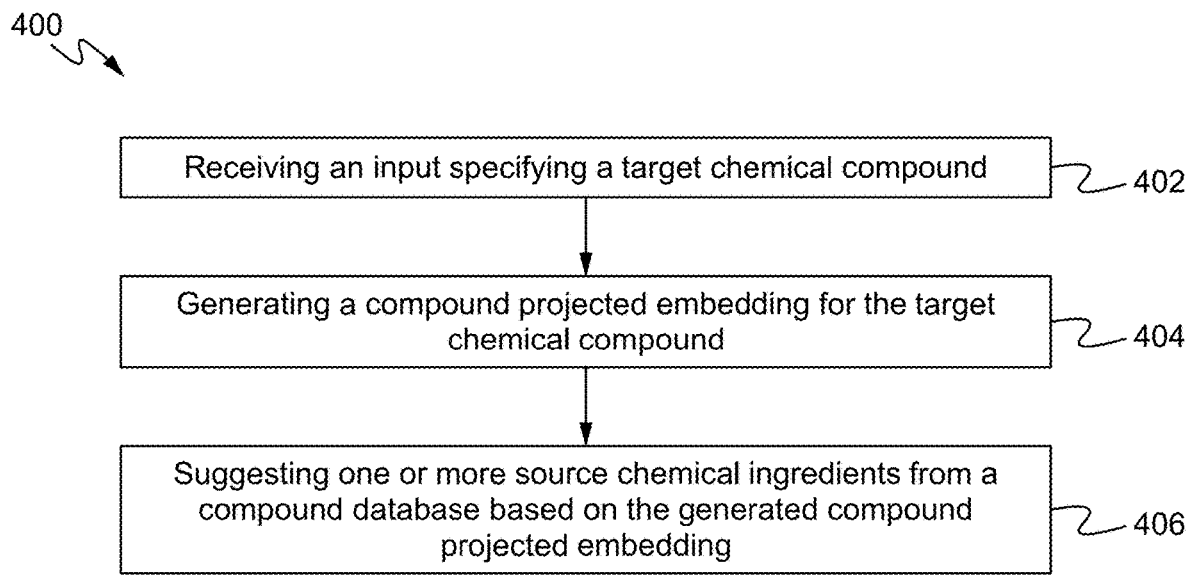
FIG. 4 illustrates an example method to suggest chemical compounds based on a target chemical compound, in accordance with some embodiments.

FIG. 4 illustrates an example method to suggest alternative chemical compounds as substitutes for a target chemical compound, in accordance with some embodiments. FIG. 4 may be used as a basis to code the method 400 as one or more computer programs or other software elements that a server computer can execute or host.

At step 402, an input specifying a target chemical compound is received from an input interface (e.g., a GUI). For example, the target chemical compound is an identified compound in a food item that is to be replaced. The target chemical compound is represented by a SMILES notation that describes the structure of the chemical compound. The target chemical compound is received by the server computer 106.

At step 404, an artificial intelligence model generates a target compound projected embedding for the target chemical compound. For example, the artificial intelligence model is the embedding generator 108. In an embodiment, the graph model 202 of the embedding generator 108 generates a target compound graph embedding for the chemical compound. Using the target compound graph embedding output from the graph model 202, the projection model 206 generates the target compound projected embedding. In an embodiment, the compound projector 208 generates the target compound projected embedding.

At step 406, one or more source chemical compounds from the compound database 124 for the target chemical compound are suggested. For example, the compound recommender 110 searches all source compound projected embeddings of source compounds to find those that may be used to recreate functional properties of the target chemical compound. In an embodiment, the compound recommender 110 uses a similarly search, such as a FAISS vector similarly search, to suggest those source chemical compounds that are similar to the target chemical compound with regards to structural and functional features. The target compound projected embedding may be compared with each source compound projected embedding from the embedding database 126. Corresponding source chemical compound of those matching source compound projected embeddings are suggested.

In an embodiment, one or more plant-based ingredients containing the one or more suggested source chemical compounds may be determined such as by referencing the source compound database 124. Each source chemical compound in the source compound database 124 is associated with one or more plant-based ingredients that contain that chemical compound. In an embodiment, the number of source chemical compounds suggested at step 406 may be specified as an input prior to step 406.

Figure 5:
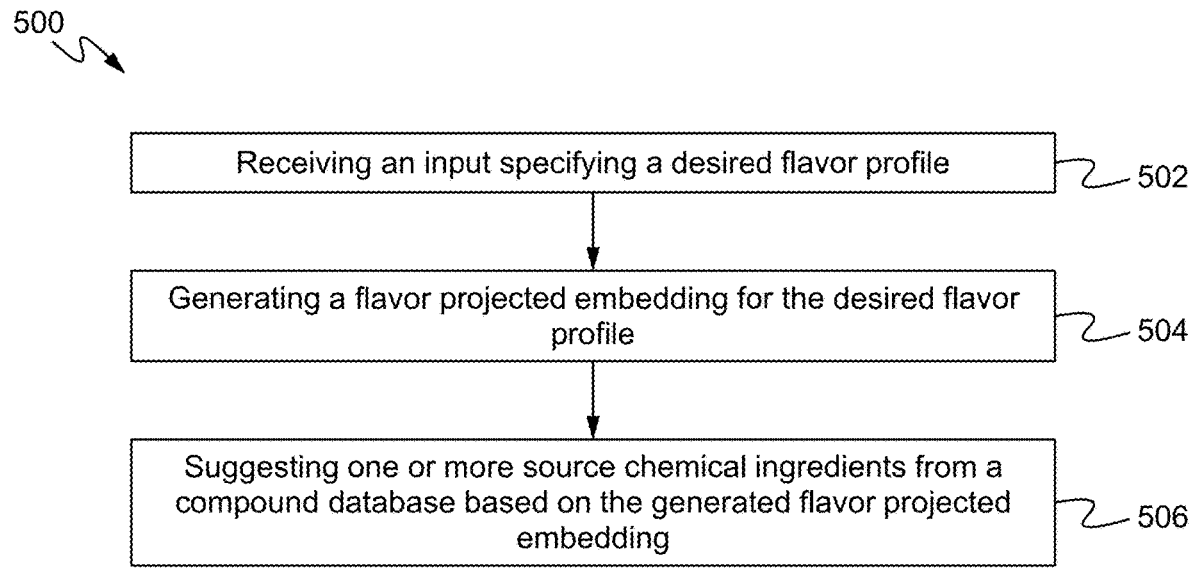
FIG. 5 illustrates an example method to suggest chemical compounds based on a desired flavor profile, in accordance with some embodiments.

FIG. 5 illustrates an example method to suggest chemical compounds with a desired flavor profile, in accordance with some embodiments. FIG. 5 may be used as a basis to code the method 500 as one or more computer programs or other software elements that a server computer can execute or host.

At step 502, an input specifying a desired flavor profile is received from an input interface (e.g., a GUI). The desired flavor profile includes one or more flavor descriptors. The desired flavor profile is received by the server computer 106.

At step 504, an artificial intelligence model generates a desired flavor projected embedding for the desired flavor profile. For example, the artificial intelligence model is the embedding generator 108. In an embodiment, the word model 204 of the embedding generator 108 generates a desired flavor word embedding for the desired flavor profile. Using the desired flavor word embedding output from the word model 204, the projection model 206 generates the desired flavor projected embedding. In an embodiment, the flavor projector 210 generates the desired flavor projected embedding.

At step 506, one or more source chemical compounds from the source compound database 124 for the desired flavor profile are suggested. For example, the compound recommender 110 searches all positive source flavor projected embeddings of source compounds to find those match the desired flavor projected embedding of the desired flavor profile. In an embodiment, the compound recommender 110 uses a similarly search, such as a FAISS vector similarly search, to compare the desired flavor projected embedding to each true source flavor projected embedding from the embedding database 126. Corresponding source compounds of those matched the source flavor projected embeddings are suggested.

In an embodiment, one or more plant-based ingredients containing the one or more suggested source chemical compounds may be determined such as by referencing the source compound database 124. Each source chemical compound in the source compound database 124 is associated with one or more plant-based ingredients that contain that chemical compound. In an embodiment, the number of source chemical compounds suggested at step 506 may be specified as an input prior to step 506.

Techniques described herein speeds up research and development by suggesting chemical compounds with desired functional properties or that may be used to recreate functional properties of target chemical compounds that are present in products, such as food items, on which to experiment and eliminates human bias in experimentation by relying only on data for suggestions. An artificial intelligence model is trained to learn relationships between source chemical compounds and their known flavor profiles. Using the learned knowledge, source chemical compounds may be suggested based on a desired flavor profile or on a target chemical compound.

4.2 Suggesting Source Ingredients

Figure 6:
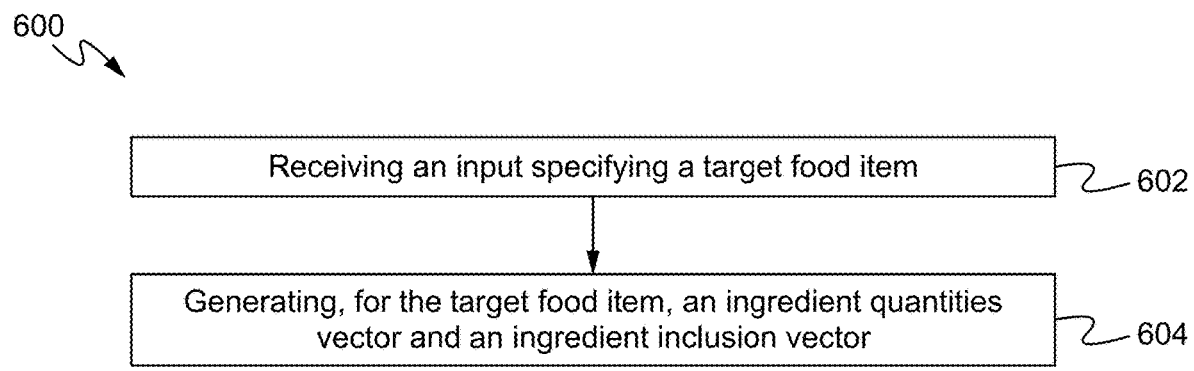
FIG. 6 illustrates an example method to suggest source ingredients based on a target food item, in accordance with some embodiments.

FIG. 6 illustrates an example method to suggest a set of source ingredients for a target food item, in accordance with some embodiments. FIG. 6 may be used as a basis to code the method 600 as one or more computer programs or other software elements that a server computer can execute or host.

At step 602, an input specifying a target food item is received from an input interface (e.g., a GUI). The target food item is a food item selected from the food item database 122 and is associated with a volatile profile and a chemical compound target food item vector. For example, the chemical compound target food item vector is a normalized chemical compound target food item vector that includes normalized concentration data based on concentrations of all relevant volatile molecules present in the target food item. The target food item is received by the server computer 106.

At step 604, a computer model generates, for the target food item, an ingredient quantities vector and an ingredient inclusion vector based on a matrix of chemical compound source ingredient vectors of all source ingredients from the source ingredient database 128. For example, the chemical compound source ingredient vectors are normalized chemical compound source ingredient vectors of all source ingredients from the source ingredient database 128. For another example, the chemical compound source ingredient vectors are enhanced chemical compound source ingredient vectors of all source ingredients from the source ingredient database 128. In an embodiment, the enhanced chemical compound source ingredient vectors are generated based on the normalized chemical compound source ingredient vectors and molecular properties, which are encoded in flavor word embeddings or flavor projected embeddings, of all chemical compounds in the source compound database 124.

The target food item may be a presented as solving a mixed integer programming optimization problem. The ingredient quantities vectors and the ingredient inclusion vector are determined by solving the optimization problem.

In an embodiment, the matrix of chemical compound source ingredient vectors (matrix V) has the dimensions |C|×|I|, wherein C is the number of chemical compounds in the source compound database 124 and I is the number of source ingredients in the source ingredient database 128. Both the ingredient quantities vector (vector Q) and the ingredients inclusion vector (vector I) have the length of |I|. The ingredient inclusion vector indicates which source ingredients to include in an optimal ingredient set and the ingredient quantities vector indicates the quantity or amount of each source ingredient such that a corresponding volatile profile of the optimal ingredient set is similar to that of the target food item. The volatile profile of the optimal ingredient set is generated by multiplying the matrix V by the vector Q and the vector I. The difference between the volatile profile for the optimal ingredient set and the volatile profile of the target food item is minimized such that the volatile profiles are as close as possible. The difference between the source ingredients in the optimal ingredient set is maximized such that similar source ingredients are avoided (not included in the set).

Techniques described herein speeds up research and development by suggesting ingredients that together have a prototype volatile flavor with functional properties for a target food item and on which to experiment and eliminate human bias in experimentation by relying only on data for suggestions. A computer model is based on solving a mixed integer programming optimization problem to find an ingredient inclusion vector and an ingredient quantities vector for the target food item.

While the techniques have been discussed with regards to compound suggestions and ingredient suggestions in food items, embodiments are not limited to this example. The techniques may be applied to compound replacement and ingredient replacement in fragrances, drugs, supplements, and other suitable products.

5.0 Hardware Overview

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques or may include digital electronic devices such as at least one application-specific integrated circuit (ASIC) or field programmable gate array (FPGA) that is persistently programmed to perform the techniques or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 7:
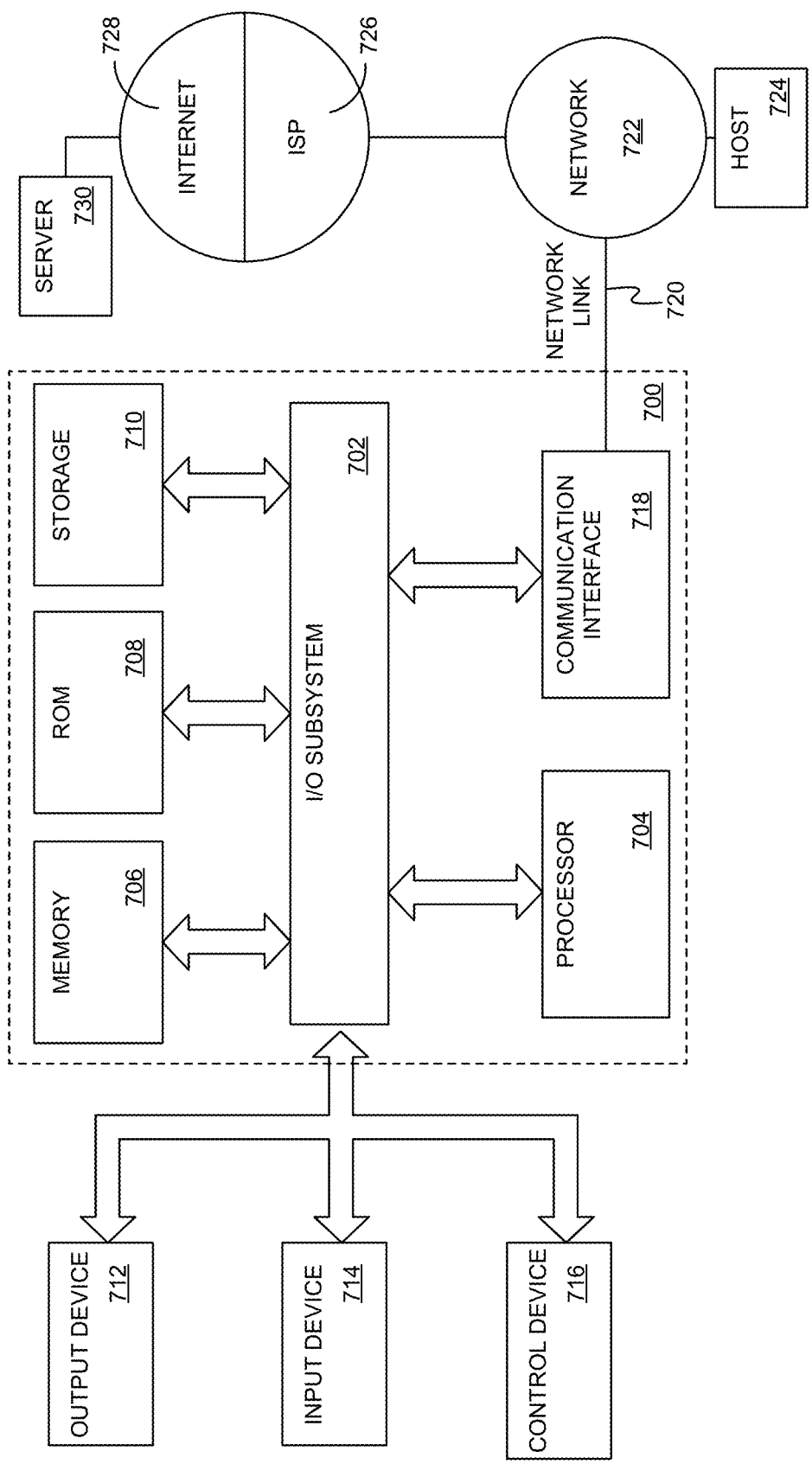
FIG. 7 illustrates a block diagram of a computing device in which the example embodiment(s) of the present invention may be embodied.

FIG. 7 is a block diagram that illustrates an example computer system with which an embodiment may be implemented. In the example of FIG. 7, a computer system 700 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 700 includes an input/output (I/O) subsystem 702 which may include a bus and/or other communication mechanism(s) for communicating information and/or instructions between the components of the computer system 700 over electronic signal paths. The I/O subsystem 702 may include an I/O controller, a memory controller and at least one I/O port. The electronic signal paths are represented schematically in the drawings, for example as lines, unidirectional arrows, or bidirectional arrows.

At least one hardware processor 704 is coupled to I/O subsystem 702 for processing information and instructions. Hardware processor 704 may include, for example, a general-purpose microprocessor or microcontroller and/or a special-purpose microprocessor such as an embedded system or a graphics processing unit (GPU) or a digital signal processor or ARM processor. Processor 704 may comprise an integrated arithmetic logic unit (ALU) or may be coupled to a separate ALU.

Computer system 700 includes one or more units of memory 706, such as a main memory, which is coupled to I/O subsystem 702 for electronically digitally storing data and instructions to be executed by processor 704. Memory 706 may include volatile memory such as various forms of random-access memory (RAM) or other dynamic storage device. Memory 706 also may be used for storing temporary variables or other intermediate information during execution of instructions to be executed by processor 704. Such instructions, when stored in non-transitory computer-readable storage media accessible to processor 704, can render computer system 700 into a special-purpose machine that is customized to perform the operations specified in the instructions.

Computer system 700 further includes non-volatile memory such as read only memory (ROM) 708 or other static storage device coupled to I/O subsystem 702 for storing information and instructions for processor 704. The ROM 708 may include various forms of programmable ROM (PROM) such as erasable PROM (EPROM) or electrically erasable PROM (EEPROM). A unit of persistent storage 710 may include various forms of non-volatile RAM (NVRAM), such as FLASH memory, or solid-state storage, magnetic disk, or optical disk such as CD-ROM or DVD-ROM and may be coupled to I/O subsystem 702 for storing information and instructions. Storage 710 is an example of a non-transitory computer-readable medium that may be used to store instructions and data which when executed by the processor 704 cause performing computer-implemented methods to execute the techniques herein.

The instructions in memory 706, ROM 708 or storage 710 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 700 may be coupled via I/O subsystem 702 to at least one output device 712. In one embodiment, output device 712 is a digital computer display. Examples of a display that may be used in various embodiments include a touch screen display or a light-emitting diode (LED) display or a liquid crystal display (LCD) or an e-paper display. Computer system 700 may include other type(s) of output devices 712, alternatively or in addition to a display device. Examples of other output devices 712 include printers, ticket printers, plotters, projectors, sound cards or video cards, speakers, buzzers or piezoelectric devices or other audible devices, lamps or LED or LCD indicators, haptic devices, actuators, or servos.

At least one input device 714 is coupled to I/O subsystem 702 for communicating signals, data, command selections or gestures to processor 704. Examples of input devices 714 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 716, which may perform cursor control or other automated control functions such as navigation in a graphical interface on a display screen, alternatively or in addition to input functions. Control device 716 may be a touchpad, a mouse, a trackball, or cursor direction keys for communicating direction information and command selections to processor 704 and for controlling cursor movement on display. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 714 may include a combination of multiple different input devices, such as a video camera and a depth sensor.

In another embodiment, computer system 700 may comprise an internet of things (IoT) device in which one or more of the output devices 712, input device 714, and control device 716 are omitted. Or, in such an embodiment, the input device 714 may comprise one or more cameras, motion detectors, thermometers, microphones, seismic detectors, other sensors or detectors, measurement devices or encoders and the output device 712 may comprise a special-purpose display such as a single-line LED or LCD display, one or more indicators, a display panel, a meter, a valve, a solenoid, an actuator or a servo.

When computer system 700 is a mobile computing device, input device 714 may comprise a global positioning system (GPS) receiver coupled to a GPS module that is capable of triangulating to a plurality of GPS satellites, determining and generating geo-location or position data such as latitude-longitude values for a geophysical location of the computer system 700. Output device 712 may include hardware, software, firmware and interfaces for generating position reporting packets, notifications, pulse or heartbeat signals, or other recurring data transmissions that specify a position of the computer system 700, alone or in combination with other application-specific data, directed toward host 724 or server 730.

Computer system 700 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 700 in response to processor 704 executing at least one sequence of at least one instruction contained in main memory 706. Such instructions may be read into main memory 706 from another storage medium, such as storage 710. Execution of the sequences of instructions contained in main memory 706 causes processor 704 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 710. Volatile media includes dynamic memory, such as memory 706. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 702. Transmission media can also take the form of acoustic or light waves, such as those generated during radio-wave and infra-red data communications.

Various forms of media may be involved in carrying at least one sequence of at least one instruction to processor 704 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 700 can receive the data on the communication link and convert the data to a format that can be read by computer system 700. For instance, a receiver such as a radio frequency antenna or an infrared detector can receive the data carried in a wireless or optical signal and appropriate circuitry can provide the data to I/O subsystem 702 such as place the data on a bus. I/O subsystem 702 carries the data to memory 706, from which processor 704 retrieves and executes the instructions. The instructions received by memory 706 may optionally be stored on storage 710 either before or after execution by processor 704.

Computer system 700 also includes a communication interface 718 coupled to bus 702. Communication interface 718 provides a two-way data communication coupling to network link(s) 720 that are directly or indirectly connected to at least one communication networks, such as a network 722 or a public or private cloud on the Internet. For example, communication interface 718 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 722 broadly represents a local area network (LAN), wide-area network (WAN), campus network, internetwork, or any combination thereof. Communication interface 718 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 718 sends and receives electrical, electromagnetic, or optical signals over signal paths that carry digital data streams representing various types of information.

Network link 720 typically provides electrical, electromagnetic, or optical data communication directly or through at least one network to other data devices, using, for example, satellite, cellular, Wi-Fi, or BLUETOOTH technology. For example, network link 720 may provide a connection through a network 722 to a host computer 724.

Furthermore, network link 720 may provide a connection through network 722 or to other computing devices via internetworking devices and/or computers that are operated by an Internet Service Provider (ISP) 726. ISP 726 provides data communication services through a world-wide packet data communication network represented as internet 728. A server computer 730 may be coupled to internet 728. Server 730 broadly represents any computer, data center, virtual machine, or virtual computing instance with or without a hypervisor, or computer executing a containerized program system such as DOCKER or KUBERNETES. Server 730 may represent an electronic digital service that is implemented using more than one computer or instance and that is accessed and used by transmitting web services requests, uniform resource locator (URL) strings with parameters in HTTP payloads, API calls, app services calls, or other service calls. Computer system 700 and server 730 may form elements of a distributed computing system that includes other computers, a processing cluster, server farm or other organization of computers that cooperate to perform tasks or execute applications or services. Server 730 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 730 may comprise a web application server that hosts a presentation layer, application layer and data storage layer such as a relational database system using structured query language (SQL) or no SQL, an object store, a graph database, a flat file system or other data storage.

Computer system 700 can send messages and receive data and instructions, including program code, through the network(s), network link 720 and communication interface 718. In the Internet example, a server 730 might transmit a requested code for an application program through Internet 728, ISP 726, local network 722 and communication interface 718. The received code may be executed by processor 704 as it is received, and/or stored in storage 710, or other non-volatile storage for later execution.

The execution of instructions as described in this section may implement a process in the form of an instance of a computer program that is being executed and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 704. While each processor 704 or core of the processor executes a single task at a time, computer system 700 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

6.0 Software Overview

FIG. 8 is a block diagram of a basic software system 800 that may be employed for controlling the operation of computing device 700. Software system 800 and its components, including their connections, relationships, and functions, is meant to be exemplary only, and not meant to limit implementations of the example embodiment(s). Other software systems suitable for implementing the example embodiment(s) may have different components, including components with different connections, relationships, and functions.

Software system 800 is provided for directing the operation of computing device 700. Software system 800, which may be stored in system memory (RAM) 706 and on fixed storage (e.g., hard disk or flash memory) 710, includes a kernel or operating system (OS) 810.

The OS 810 manages low-level aspects of computer operation, including managing execution of processes, memory allocation, file input and output (I/O), and device I/O. One or more application programs, represented as 802A, 802B, 802C . . . 802N, may be "loaded" (e.g., transferred from fixed storage 710 into memory 706) for execution by the system 800. The applications or other software intended for use on device 800 may also be stored as a set of downloadable computer-executable instructions, for example, for downloading and installation from an Internet location (e.g., a Web server, an app store, or other online service).

Software system 800 includes a graphical user interface (GUI) 815, for receiving user commands and data in a graphical (e.g., "point-and-click" or "touch gesture") fashion. These inputs, in turn, may be acted upon by the system 800 in accordance with instructions from operating system 810 and/or application(s) 802. The GUI 815 also serves to display the results of operation from the OS 810 and application(s) 802, whereupon the user may supply additional inputs or terminate the session (e.g., log off).

OS 810 can execute directly on the bare hardware 820 (e.g., processor(s) 704) of device 700. Alternatively, a hypervisor or virtual machine monitor (VMM) 830 may be interposed between the bare hardware 820 and the OS 810. In this configuration, VMM 830 acts as a software "cushion" or virtualization layer between the OS 810 and the bare hardware 820 of the device 700.

VMM 830 instantiates and runs one or more virtual machine instances ("guest machines"). Each guest machine comprises a "guest" operating system, such as OS 810, and one or more applications, such as application(s) 802, designed to execute on the guest operating system. The VMM 830 presents the guest operating systems with a virtual operating platform and manages the execution of the guest operating systems.

In some instances, the VMM 830 may allow a guest operating system to run as if it is running on the bare hardware 820 of device 700 directly. In these instances, the same version of the guest operating system configured to execute on the bare hardware 820 directly may also execute on VMM 830 without modification or reconfiguration. In other words, VMM 830 may provide full hardware and CPU virtualization to a guest operating system in some instances.

In other instances, a guest operating system may be specially designed or configured to execute on VMM 830 for efficiency. In these instances, the guest operating system is "aware" that it executes on a virtual machine monitor. In other words, VMM 830 may provide para-virtualization to a guest operating system in some instances.

The above-described basic computer hardware and software is presented for purpose of illustrating the basic underlying computer components that may be employed for implementing the example embodiment(s). The example embodiment(s), however, are not necessarily limited to any particular computing environment or computing device configuration. Instead, the example embodiment(s) may be implemented in any type of system architecture or processing environment that one skilled in the art, in light of this disclosure, would understand as capable of supporting the features and functions of the example embodiment(s) presented herein.

7.0 Other Aspects of Disclosure

Although some of the figures described in the foregoing specification include flow diagrams with steps that are shown in an order, the steps may be performed in any order, and are not limited to the order shown in those flowcharts. Additionally, some steps may be optional, may be performed multiple times, and/or may be performed by different components. All steps, operations and functions of a flow diagram that are described herein are intended to indicate operations that are performed using programming in a special-purpose computer or general-purpose computer, in various embodiments. In other words, each flow diagram in this disclosure, in combination with the related text herein, is a guide, plan or specification of all or part of an algorithm for programming a computer to execute the functions that are described. The level of skill in the field associated with this disclosure is known to be high, and therefore the flow diagrams and related text in this disclosure have been prepared to convey information at a level of sufficiency and detail that is normally expected in the field when skilled persons communicate among themselves with respect to programs, algorithms and their implementation.

In the foregoing specification, the example embodiment(s) of the present invention have been described with reference to numerous specific details. However, the details may vary from implementation to implementation according

What is claimed is:

1. A computer-implemented method of suggesting source ingredients, comprising:
   obtaining a compound concentration source ingredient vector for each source ingredient of a plurality of source ingredients in a source ingredient database,
   wherein the compound concentration source ingredient vector of each source ingredient of the plurality of source ingredients includes, for a respective source ingredient, concentration data of a plurality of chemical compounds in a chemical compound database;
   receiving a request that identifies a particular product;
   applying a computer model to an aggregate of compound concentration source ingredient vectors of the plurality source ingredients to generate a plurality of vectors including an ingredient quantities vector and an ingredient inclusion vector for the particular product,
   wherein the ingredient inclusion vector identifies one or more source ingredients of the plurality of source ingredients to include in a candidate ingredient set and the ingredient quantities vector identifies an amount of each of the one or more source ingredients;
   suggesting at least one source ingredient of the one or more source ingredients in the candidate ingredient set in response to receiving the request.

2. The method of claim 1, further comprising obtaining a compound concentration product vector for each product of a plurality of products in a product database, wherein the compound concentration product vector of each product of the plurality of products includes, for a respective product, concentration data of the plurality of chemical compounds in the chemical compound database.

3. The method of claim 2, wherein a linear combination of the one or more ingredients in the candidate ingredient set closely resembles a compound concentration product vector of the particular product.

4. The method of claim 2, wherein the compound concentration product vector for each product of the plurality of products in the product database is a normalized compound concentration product vector generated from gas chromatography mass spectrometry (GCMS) data.

5. The method of claim 2, wherein the compound concentration source ingredient vector for each source ingredient of the plurality of source ingredients in the source ingredient database is either a normalized compound concentration source ingredient vector generated from gas chromatography mass spectrometry (GCMS) data or an enhanced compound concentration source ingredient vector generated from the normalized compound concentration source ingredient vector and chemical compound descriptors.

6. The method of claim 5, wherein the chemical compound descriptors are encoded in flavor embeddings generated by an artificial intelligence model,
   wherein the artificial intelligence model, including at least one neural network, is trained on first digital data representing a first plurality of chemical compounds, second digital data representing a first plurality of true flavor profiles of the first plurality of chemical compounds, and third digital data representing a first plurality of false flavor profiles for the first plurality of chemical compounds,
   wherein each chemical compound in the first plurality of chemical compounds is associated with a true flavor profile in the first plurality of true flavor profiles and with one or more false flavor profiles in the first plurality of false flavor profiles,
   wherein the artificial intelligence model is trained, for each chemical compound in the first plurality of chemical compounds, to align a compound projected embedding of a respective chemical compound with a positive flavor projected embedding of the true flavor profile associated with the respective chemical compound in a joint vector space, and to distance the compound projected embedding from one or more negative flavor projected embeddings of the one or more false flavor profiles associated with the respective chemical compound in the joint vector space.

7. The method of claim 1, wherein the particular product is presented as a mixed integer programming optimization problem to the computer model, wherein an objective function of the computer model is to maximize profile similarity between the target product and the one or more ingredients in the candidate ingredient set.

8. One or more non-transitory computer-readable storage media storing one or more instructions programmed for suggesting source ingredients, when executed by one or more computing devices, cause:
   obtaining a compound concentration source ingredient vector for each source ingredient of a plurality of source ingredients in a source ingredient database,
   wherein the compound concentration source ingredient vector of each source ingredient of the plurality of source ingredients includes, for a respective source ingredient, concentration data of a plurality of chemical compounds in a chemical compound database;
   receiving a request that identifies a particular product;
   applying a computer model to an aggregate of compound concentration source ingredient vectors of the plurality source ingredients to generate a plurality of vectors including an ingredient quantities vector and an ingredient inclusion vector for the particular product,
   wherein the ingredient inclusion vector identifies one or more source ingredients of the plurality of source ingredients to include in a candidate ingredient set and the ingredient quantities vector identifies an amount of each of the one or more source ingredients;
   suggesting at least one source ingredient of the one or more source ingredients in the candidate ingredient set in response to receiving the request.

9. The one or more non-transitory computer-readable storage media of claim 8, wherein the instructions, when executed by the one or more computing devices, further cause obtaining a compound concentration product vector for each product of a plurality of products in a product database, wherein the compound concentration product vector of each product of the plurality of products includes, for a respective product, concentration data of the plurality of chemical compounds in the chemical compound database.

10. The one or more non-transitory computer-readable storage media of claim 9, wherein a linear combination of the one or more ingredients in the candidate ingredient set closely resembles a compound concentration product vector of the particular product.

11. The one or more non-transitory computer-readable storage media of claim 9, wherein the compound concentration product vector for each product of the plurality of products in the product database is a normalized compound concentration product vector generated from gas chromatography mass spectrometry (GCMS) data.

12. The one or more non-transitory computer-readable storage media of claim 9, wherein the compound concentration source ingredient vector for each source ingredient of the plurality of source ingredients in the source ingredient database is either a normalized compound concentration source ingredient vector generated from gas chromatography mass spectrometry (GCMS) data or an enhanced compound concentration source ingredient vector generated from the normalized compound concentration source ingredient vector and chemical compound descriptors.

13. The one or more non-transitory computer-readable storage media of claim 12, wherein the chemical compound descriptors are encoded in flavor embeddings generated by an artificial intelligence model.

14. The one or more non-transitory computer-readable storage media of claim 9, wherein the particular product is presented as a mixed integer programming optimization problem to the computer model, wherein an objective function of the computer model is to maximize profile similarity between the target product and the one or more ingredients in the candidate ingredient set.

15. A computing system comprising:
one or more computer systems comprising one or more hardware processors and storage media; and
instructions stored in the storage media and which, when executed by the computing system, cause the computing system to perform:
obtaining a compound concentration source ingredient vector for each source ingredient of a plurality of source ingredients in a source ingredient database, wherein the compound concentration source ingredient vector of each source ingredient of the plurality of source ingredients includes, for a respective source ingredient, concentration data of a plurality of chemical compounds in a chemical compound database;
receiving a request that identifies a particular product;
applying a computer model to an aggregate of compound concentration source ingredient vectors of the plurality source ingredients to generate a plurality of vectors including an ingredient quantities vector and an ingredient inclusion vector for the particular product,
wherein the ingredient inclusion vector identifies one or more source ingredients of the plurality of source ingredients to include in a candidate ingredient set and the ingredient quantities vector identifies an amount of each of the one or more source ingredients;
suggesting at least one source ingredient of the one or more source ingredients in the candidate ingredient set in response to receiving the request.

16. The computing system of claim 15, wherein the instructions, when executed by the computing devices, further cause obtaining a compound concentration product vector for each product of a plurality of products in a product database, wherein the compound concentration product vector of each product of the plurality of products includes, for a respective product, concentration data of the plurality of chemical compounds in the chemical compound database.

17. The computing system of claim 16, wherein a linear combination of the one or more ingredients in the candidate ingredient set closely resembles a compound concentration product vector of the particular product.

18. The computing system of claim 16, wherein the compound concentration product vector for each product of the plurality of products in the product database is a normalized compound concentration product vector generated from gas chromatography mass spectrometry (GCMS) data.

19. The computing system of claim 16, wherein the compound concentration source ingredient vector for each source ingredient of the plurality of source ingredients in the source ingredient database is either a normalized compound concentration source ingredient vector generated from gas chromatography mass spectrometry (GCMS) data or an enhanced compound concentration source ingredient vector generated from the normalized compound concentration source ingredient vector and chemical compound descriptors.

20. The computing system of claim 16, wherein the chemical compound descriptors are encoded in flavor embeddings generated by an artificial intelligence model.

* * * * *